United States Patent
Dong et al.

(10) Patent No.: US 6,407,088 B1
(45) Date of Patent: Jun. 18, 2002

(54) METHOD OF ANALGESIA

(75) Inventors: Qingbin Dong, Nanning City (CN); Frank Hay Kong Shum, North Point (HK)

(73) Assignee: Wex Medical Instrumentation Co., Ltd., North Point (HK)

( * ) Notice: Subject to any disclaimer, the term of this patent is extended or adjusted under 35 U.S.C. 154(b) by 0 days.

(21) Appl. No.: 09/695,053

(22) Filed: Oct. 25, 2000

(30) Foreign Application Priority Data

Sep. 18, 2000 (CN) .......................... 00 1 24517

(51) Int. Cl.7 ..................... A61K 31/33; A61K 31/505; A61K 31/44
(52) U.S. Cl. ................. 514/183; 514/257; 514/267; 514/282
(58) Field of Search ................ 514/183, 257, 514/267, 282

(56) References Cited

U.S. PATENT DOCUMENTS

| 4,022,899 A | | 5/1977 | Adams et al. | |
| 4,029,793 A | | 6/1977 | Adams et al. | |
| 5,846,975 A | * | 12/1998 | Pan et al. | 514/282 |
| 6,030,974 A | * | 2/2000 | Schwartz et al. | 514/267 |

OTHER PUBLICATIONS

Bower et al., Nonprotein Neurotoxins, Clin. Toxicol. 18 (7) :813–863 (1981).
C.Y. Kao, Pharmacological Reviews, vol. 18, No. 2, 997–1049 (1966).
Kao, C.Y. and Fuhrman, F.A., J. Pharmacol. 140: 31–40 (1963).
Zapata et al., Pain 72:41–49 (1997).
M.S. Wallace, Clin. J. Pain, vol. 16:S80–S85 (2000).
Yotsu, M. et al., Agric. Biol. Chem., 53 (3) :893–895 (1989).

* cited by examiner

Primary Examiner—Raymond Henley, Jr.
(74) Attorney, Agent, or Firm—Birch, Stewart, Kolasch & Birch LLP

(57) ABSTRACT

This invention relates to a method of producing analgesia in a mammal experiencing pain by systemically administering an effective amount of a composition comprising essentially of a sodium channel blocking compound, in a suitable pharmaceutical vehicle, to alleviate the pain.

21 Claims, No Drawings

METHOD OF ANALGESIA

FIELD OF THE INVENTION

This invention presents a method of alleviating pain, such as central pain, pain arising from cancer and phantom limb pain, by systemic administration of sodium channel blocking compounds, including tetrodotoxin and saxitoxin.

BACKGROUND OF THE INVENTION

Pain is a sensation that hurts. It may cause discomfort or distress or agony. It may be steady or throbbing. It may be stabbing, aching, or pinching. However pain is felt, only the person experiencing pain can describe it or define it. Because pain is so individual, pain cannot be truly evaluated by any third person.

The World Health Organization (WHO) recognizes a "Three-step Analgesic Ladder" for pharmacologic management of pain. The ladder begins with relatively low doses of low-potency analgesics and progresses to higher doses of more potent compounds. The three steps involve use of:

Nonopioid analgesics with or without coanalgesics, such as Nonsteroid Anti-inflammatory Drugs (NSAIDs);

Lower-potency opioids with or without coanalgesics as pain persists or increases to moderate levels;

High-potency opioids with or without nonopioid coanalgesics as pain persists or increases to severe levels.

Use of opioid analgesics, even for treatment of severe pain, is controversial in the medical community, due to the possibility of addiction. See, e.g. S. E. Weitz et al., New Jersey Medicine, Vol. 97: 63–67 (2000).

Tetrodotoxin is a nonprotein neurotoxin that is found in multiple diverse animal species, including puffer fish, goby fish, newt, frogs and the blue-ringed octopus.

Tetrodotoxin can be obtained from the ovaries and eggs of several species of pufferfish of the suborder Gymnodontes. Tetrodotoxin is the agent for poisoning occurring from the consumption of ill-prepared fugu fish in sushi bars. Tetrodotoxin can also be obtained from California newts of the genus taricha.

One biological activity of tetrodotoxin is binding of the alpha subunit of neuronal sodium channels. Tetrodotoxin has a chemical formula of $C_{11}H_{17}N_3O_8$, and has a molecular weight of 319.28. The Merck Index, $10^{th}$ Ed. (1983), states tetrodotoxin is the generic name for the compound octahydro-12-(hydroxymethyl)-2-imino-5,9:7,10a-dimethano-10aH-(1,3)dioxocino(6,5-d)-pyrimidine-4,7,10,11,12-pentol, which has the following structure:

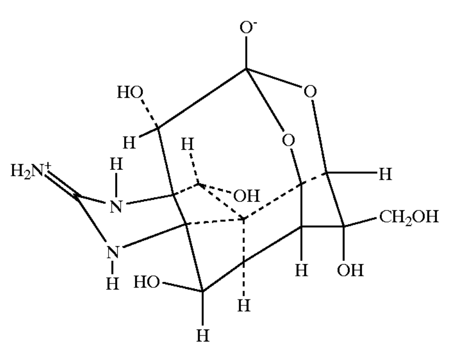

The Merck Index, $10^{th}$ Ed. (1983), states tetrodotoxin is also referred to as maculotoxin, spheroidine, tarichatoxin, tetrodontoxin, fugu poison and TTX.

According to U.S. Pat. No. 6,030,974, "tetrodotoxin" or "TTX" refers to the amino perhydroquinazoline compounds having the molecular formula $C_{11}H_{17}N_3O_8$ and to derivatives thereof, including but not limited to anhydrotetrodotoxin, tetrodaminotoxin, methoxytetrodotoxin, ethoxytetrodotoxin, deoxytetrodotoxin and tetrodonic acid (Kao). Examples of TTX analogs include novel TTX analogs isolated from various organisms, as well as those that are partially or totally chemically synthesized. See e.g., Yotsu, M. et al. Agric. Biol. Chem., 53(3):893–895 (1989). Such analogs bind to the same site on the alpha subunit of sodium channels as does TTX.

Adams, et al., U.S. Pat. Nos. 4.022,899 and 4,029,793 pertain to a local anesthetic composition comprising a mixture in a pharmaceutically acceptable carrier of a particular toxin, namely tetrodotoxin or desoxytetrodotoxin, and another compound, generally a conventional local anesthetic compound or a similar compound having nerve-blocking properties. The conventional local anesthetic can be an aminoacylanilide such as lidocaine, an aminoalkylbenzoate such as procaine, cocaine, an amino carbamate such as diperodon, a N-phenylamidine such as phenacine, a N-aminoalkyl amide such as dibucaine, an aminoketone such as falicain, or an aminoether such as pramoxine.

According to U.S. Pat. No. 6,030,974, "saxitoxin" or "STX" refers to a compound comprising a tetrahydropurine moiety composed of two guanidine units fused together in a stable azaketal linkage, having a molecular formula $C_{10}H_{17}N_7O_4$, (mol. wt. 299.30) and to derivatives thereof, including but not limited to hydroxysaxitoxins and neosaxitoxin. See Bower et al., Nonprotein Neurotoxins, Clin. Toxicol. 18(7):813–863 (1981).

Tetrodotoxin and its significance in the study of excitation phenomena has been reviewed by C. Y. Kao, Pharmacological Reviews, Vol. 18, No. 2, 997–1049 (1966). Kao notes that one of the most prominent actions of tetrodotoxin in the whole animal is a rapidly progressive and marked weakening of all voluntary muscles, including the respiratory muscles (Kao at 1016). However, Kao notes that specific action of tetrodotoxin on the central nervous system is debatable (Kao at 1022, line 3).

Pan et al., U.S. Pat. No. 5,846,975, discloses the use of amino hydrogenated quinazoline compounds, such as tetrodotoxin, for treating drug dependence in humans. Tetrodotoxin was shown to be effective against withdrawal symptoms from opium, heroin, morphine, cocaine, amphetamine, dolandin, dihydroetorphine and methadone. Amounts effective for relieving withdrawal symptoms are described in this patent.

Tetrodotoxin can be used as a local anesthetic and is ten thousand times more powerful than commonly used local non-narcotics, as is discussed by C. Y. Kao and F. A. Fuhrman, J. Pharmacol., 140, 31–40 (1963). Tetrodotoxin preparations in combination with other widely used anesthetics have been noted in U.S. Pat. Nos. 4,022,899 and 4,029,793.

U.S. Pat. No. 6,030,974 describes a method of producing local anesthesia in a mammal experiencing pain in an epithelial tissue region. The method includes topically administering to the region, in a suitable pharmaceutical vehicle, an effective dose of a long-acting sodium channel blocking compound. The sodium channel blocking compound of U.S. Pat. No. 6,030,974 can be a formulation of tetrodotoxin or saxitoxin at a concentration of between 0.001–10 mM.

Zapata et al., Pain 72:41–49 (1997) discusses the utilization of tetrodotoxin for the inhibition of neuropathic ectopic activity in neuromas, dorsal root ganglia and dorsal horn neurons. The neuronal activity arises from neuroma caused by mechanical, chemical or ischemic injury. The effect of intravenously administered TTX on the neuronal induction by sciatic nerves in male rats was researched. However, the dosages and effects studied by Zapata et al. were applied to animals under anesthesia and artificial ventilation, thus these doses are above the maximal tolerated dose and the administration was under conditions that are not applicable to the presently intended clinical use of tetrodotoxin.

Although there has been extensive research into the effectiveness of TTX and its derivatives as a sodium channel blocker and local anesthetic, systemic administration of pure TTX as an analgesic has never been disclosed. The potential for TTX to alleviate pain arising from the activity in the central nervous system, rather from the stimulation of peripheral nerves does not seem to have been described.

The alleviation of chronic severe pain, such as that arising from cancer and "phantom limb pain" is an important topic in modern medicine. Cancer is highly pervasive in the human population.

A person suffering from cancer frequently experiences severe pain. This pain can also be known as central pain or chronic pain. However, a patient need not be suffering from cancer to experience central pain or chronic pain. A related type of pain is phantom limb pain. These types of pain have been treated by opiates such as morphine. A drawback of the opiate analgesia is the addictive nature of the opiates.

Acute local pain can arise, for example, from toothaches, eye irritation, inflammation in a nervous tissue region, canker sores, genital ulcers, and pain in epithelial tissues caused by burns, surgery or soreness.

Perception of pain can also be divided into three areas; acute nociceptive processing, facilitated pain arising from persistent afferent input (as after tissue injury) and neuropathic pain that arises from altered processing after nerve injury.

Some sodium channel blocking compounds, e.g. lidocaine and mexiletine, typically used as local anesthetics, have also been administered systemically. These compounds seem to be marginally effective in blocking acute nociceptive processing, and there is some effect observable upon spinal processing and substance P release, indicating effects on facilitated pain. However, the effective doses are above the maximum tolerated dose and thus side effects have precluded use of these compounds as systemic analgesics. Furthermore, sodium channel blockers have previously been found entirely ineffective in managing neuropathic pain. See, M. S. Wallace, "Calcium and Sodium channel blocking compounds for the Treatment of Pain", Clin. J. Pain, Vol. 16: S80–S85 (2000).

Several sodium channel blockers such as lidocaine and carbamazepine have been used in the treatment of neuropathic pain and trigeminal neuralgia. These substances may block sodium channels to abolish abnormal peripheral nerves activity at concentrations which do not block nerve conduction. Since it may cause severe damage to the function of liver, however, carbamazepine should be restricted from being used on women in the early stage of pregnancy and during breasting period, and should be used with caution on older people and those who have glaucoma or severe angiocardiopathy. On the other hand, lidocaine has such an excitation effect on the central nerve system that it can cause tremor, shivering and clonic spasm. Therefore, these two drugs are considered inappropriate to promote as new analgesics for systemic use. This has stimulated interest in developing other sodium channel blocking drugs.

In 1998, Rabert et al demonstrated that the existence of more than one type of sodium channels in rat dorsal root ganglion (DRG) sensory neurons. These sodium channels have been distinguished on the basis of a differential sensitivity to TTX: a TTX-sensitive sodium channel (TTX-S) is blocked by TTX with $IC_{50}$ of 1–20 nM. A TTX-resistant sodium channel (TTX-R) is blocked by TTX with an $IC_{50}$ of ~100 $\mu$M. The rBIIA, rBII1, rSKM1, rPN1 and rPN4 sodium channels are all TTX-S, whereas rPN3/SNS sodium channels are TTX-R. There are also two types of sodium channels in human DRG sensory neurons: hPN1 is a TTX-S channel and hPN3 is a TTX-R channel blocked by TTX with an $IC_{50}$=80 $\mu$M. Rabbert also showed that sodium channels in mammalian DRG sensory neurons express at least two sodium currents: a TTX-sensitive current (TTX-$SI_{Na}$) with rapid inactivation kinetics and a TTX-resistant current (TTX-$RI_{Na}$) with slower inactivation kinetics. The biological role of the two sodium currents has not been delineated whereas numerous studies indicated that the properties of the TTX-$RI_{Na}$ currents in dorsal root ganglia appear well suited to contribute to the sustained neuronal firing characteristic of most neuropathic pain conditions.

Nociceptors are primary afferent neurons that respond to noxious or potentially tissue-damaging stimuli and are unique among sensory neurons because they can be sensitized. The decrease in the threshold and increase in the response to a constant stimulus that are characteristic of nociceptor sensitization are thought to underlie the hyperalgesia or tenderness associated with tissue injury. Agents released at the site of tissue injury sensitize nociceptors by initiating a cascade of event that likely results in a change in ionic conductance of the nociceptor peripheral terminal. Small-diameter sensory neurons in the DRG are known to express a TTX-R channel activity. A variety of inflammatory insults and direct damage to sensory neuron fibers produce a decrease in the thresholds of activation of sensory neurons, while prolonged activation of sensory neurons can lead to central sensitization to noxious input within the spinal cord. When sensory neurons were highly excited, activity of sodium channels and voltage-gated sodium current were increased significantly. Recent numerous studies suggest that increase of TTX-$RI_{Na}$ may play a significant role in the hyperexcitability of sensory neurons. Increased TTX-$RI_{Na}$ may contribute to diverse acute and chronic pain such as neuropathic pain and neuroma pain which were induced by inflammation and nerve damage. Patch-clamp electrophysiological techniques have been used to study the effects of hyperalgesic agents that modulate TTX-$RI_{Na}$ at primary culture DRG neurons. Evidence suggests that prostaglandin $E_2$ ($PGE_2$), adenosine and serotonin increase the magnitude of TTX-$RI_{Na}$, shift its conductance-voltage relationship in a hyperpolarized direction, and increase its rate of activation and inactivation. In contrast, thromboxane $B_2$, a cyclooxygenase product which does not produce hyperalgesia, does not affect TTX-$RI_{Na}$. These results suggest that an increase in TTX-$RI_{Na}$ underlies the increase in nociceptor neuronal sensitization induced by hyperalgesic agents. Intratheacal administration of antisense and sense oligodeoxynucleotides ($ODN_S$), which were directed against a unique sequence of the rPN3 or SNS were used to examine the role of these channels in $PGE_2$-induced hyperalgesia. Only antisense ODNs led to a decrease in $PGE_2$-induced hyperalgesia. $PGE_2$-induced hyperalgesia was partially recovered 4 days after the last antisense ODN injection, and was fully recovered within 7 days. Antisense ODNs selectively and significantly reduced TTX-$RI_{Na}$ current density in cultured sensory neurons. These finding support the hypothesis that modulation of TTX-$RI_{Na}$ contributes to inflammatory hyperalgesia.

Novakovis et al by their immunohistochemical studies, showed that sodium channels, especially PN3 channels, accumulated at the site of injury. The subcellular distribution of PN3 channels also changed after neuropathic injury, and nerve conduction was significantly altered. Sodium channel anterograde axonal transport is completely blocked in neuropathic pain and neuroma pain models, and is significantly reduced in the chronic constriction injury model of neuropathic pain (CCI). Because sodium channels, presumably including TTX-R channels, are constantly being transported to peripheral terminals, alterations in axonal transport ultimately result in channel accumulation at the injury site. Nerve degeneration and subsequent regeneration of many new axonal sprouts could be observed at the injury site in the CCI and neuroma models. Many of these new sprouts appear to be immunopositive for PN3. The overaccumulation of sodium channels occurs in regeneration fibers. Sensitization of CNS is an important characteristic of neuropathic pain. Establishment and maintainance of CNS sensitization relies on sense information conducted by nociceptor nerve fibers. In the pain state, because TTX-R channels are involved in coding information of pain sense, TTX-R channels are thought to play an important role in central perception of pain input.

In summary, modulation of TTX-R sodium channels is thought to play a role in the sensitization of nociceptors in the persistent pain state. The tissue distribution of TTX-R channels is restricted to a subpopulation of sensory neurons with properties of nociceptors. It is possible that designing a pharmacotherapeutic agent that selectively blocks TTX-R channels will be effective for pain relief. hPN3 may prove to be a valuable target for a therapeutic agent for treatment of acute and chronic pain.

TTX blocking of TTX-R channels may contribute to antinociceptive action of TTX in animals. In animal models of pain, neuromas, neuropathic pain or persistent dysesthesis initiated by artificial damage to peripheral sensory nerves produces ectopic discharges originating at both injury site and related dorsal root ganglia, and consequently hyperexcitability in associated dorsal horn (DH) neurons of spinal cord. TTX inhibits neuropathic ectopic activity in neuromas, DRG, and DH neurons in a dose-dependent pattern. However, at present the relative contribution of TTX-S and TTX-R channels to the generation of ectopic discharges in neuromas, DRG, and DH neurons is not clear.

TTX produces antinociceptive action at dose levels that do not significantly change behavior of animals. However, TTX at these dose levels does not modulate distribution and function of sodium channels, nor does TTX fully block nerve conduction in various types of pain conditions. These results suggest that TTX may unexpectedly act on TTX-R sodium channels to produce an antinociceptive action.

SUMMARY OF THE INVENTION

Pain may be acute or chronic. Acute pain can be severe, but lasts a relatively short time. It is usually a signal that body tissue is being injured in some way, and the pain generally disappears when the injury heals. Chronic pain may range from mild to severe, and it is present to some degree for long periods of time. Chronic pain often arises without any detectable injury.

TTX is also effective for alleviating acute pain induced by mechanical and chemical stimulation, and inflammation.

Tetrodotoxin (TTX) has been shown to be effective on pains produced by liver cancer, rectal cancer, leiomyosarcoma, bone cancer, stomach cancer, lymphatic cancer, esophageal cancer and other major cancer types. TTX is also effective on central pain, chronic pain and phantom limb pain.

Tetrodotoxin is effective on all severe chronic pains. Tetrodotoxin is capable of generating analgesia in a mammal experiencing acute or chronic pain. The method of the present invention includes systemically (generally, to the whole body) administering, in a suitable pharmaceutical vehicle, an effective dose of a long-acting sodium channel blocking compound, i.e. tetrodotoxin.

TTX is administered in a dosage range of 0.1–1 μg/kg. TTX is administered in a schedule of up to 4 doses per day over a time period of 3 days. Frequently the effectiveness of the dose lasts for up to 20 days.

The purity of TTX is usually 96% or greater.

Saxitoxin (STX) is a highly selective and highly active sodium channel blocking compound. According to U.S. Pat. No. 6,030,974, both TTX and STX specifically bind to a site on an extracellular region of a sodium channel alpha subunit. The site is in either an SS1 region or an SS2 region (Evans, Tetrodotoxin, Saxitoxin, and Related Substances: Their Applications in Neurobiology, International Review of Neurobiology, Vol. 15, pp. 83–166, 1972, Academic Press).

The $LD_{50}$ of saxitoxin for mice by intraperitoneal injection is 10 μg/kg (Schantz, E. J., McFarren, E. F., Schaeffer, M. L. and Lewis, K. H.: Purified shellfish poison for bioassay standardization. J. Assoc. Official Agricul. Chemist. 41: 160–168, 1958.); in rats, the intraperioneal $LD_{50}$ is 10.5 microgram/kg (Watts, J. S., DaCosta, F. and Reilly, J.: Some factors influencing the action of paralytic shellfish poison in rats. Fed. Proc. 24: 392, 1965); the estimated human lethal dose (oral) of between 300 μg to 1.0 mg (Bower et al., Clin. Toxicol., 18(7):813–863, 1981).

In view of the similar mode of action and toxicity of TTX and STX, dosages of the two toxins for analgesia are also similar.

DETAILED DESCRIPTION OF THE INVENTION

Pain can originate for many reasons. A familiar cause is trauma, such as a sprain or muscle injury or broken bone, or from surgery. Pain due to inflammation, such as a toothache, is also familiar to many. Headache is a common experience and arises often for unknown reasons.

Cancer patients may have pain for a variety of reasons. It may be due to the effects of the cancer itself, or it could result from treatment methods. For example, after surgery a person feels pain as a result of the operation itself. Not all people with cancer have pain, and those who do are not in pain all the time.

Cancer pain may depend on the type of cancer, the stage (extent) of the disease, and the patient's pain threshold (tolerance for pain). Cancer pain that lasts a few days or longer may result from:

The tumor causing pressure on organs, nerves, or bone.

Poor blood circulation because the cancer has blocked blood vessels.

Blockage of an organ or tube in the body.

Metastasis—cancer cells that have spread to other sites in the body.

Infection or inflammation.

Side effects from chemotherapy, radiation therapy, or surgery.

Stiffness from inactivity.

Psychological responses to illness such as tension, depression, or anxiety.

The difference between acute and chronic pain is discussed by Joseph T. Dipiro, "Pharmacotherapy: A Pathophysiologic Approach", Third Edition, Appleton & Lange (1997) p. 1263. Dipiro explains that acute pain may be a useful physiologic process warning individuals of disease states and potentially harmful situations. Unfortunately, severe, unremitting, undertreated pain, when it outlives its biologic usefulness, can produce many deleterious effects such as psychological problems. When pain is not effectively treated, the stress and concurrent reflex reactions often cause hypoxia, hypercapnia, hypertension, excessive cardiac activity, and permanent emotional difficulties. The problems associated with these reactions range from prolonged recovery time to death.

Under normal conditions, acute pain quickly subsides as the healing process decreases the pain-producing stimuli. However, in some instances pain may persist for months to years, leading to a chronic pain state with features quite different from those of acute pain. Typically, chronic pain is divided into four subtypes: pain that persists beyond the normal healing time for an acute injury, pain related to a chronic disease, pain without identifiable organic cause, and pain that involves both the chronic and acute pain associated with cancer. Patients in chronic pain often develop severe psychological problems caused by fear and memory of past pain. In additional, chronic pain patients may develop dependence and tolerance to analgesics, have trouble sleeping, and more readily react to environmental changes that can intensify pain and the pain response. Distinguishing between chronic and acute pain states is very important because of differing management techniques.

Acute and chronic pain can also be classified by duration. Acute pain lasts or is anticipated to last less than 1 month, e.g., postoperative pain. Chronic pain is usually defined as pain persisting more than 1 month, e.g., cancer pain and phantom limb pain.

The National Institute of Neurological Disorders and Stroke, National Institutes of Health (http://healthlink/mcw.edu/article/921391401.html; Jun. 29, 2000) describes central pain syndrome as a neurological condition caused by damage specifically to the central nervous system (CNS)—brain, brainstem, or spinal cord. The pain is steady and is usually described as a burning, aching, or cutting sensation. Occasionally there may be brief, intolerable bursts of sharp pain.

Central pain is characterized by a mixture of pain sensations, the most prominent being constant burning. Mingled with the burning are sensations of cold, "pins and needles" tingling, and nerve proximity (like that of a dental probe on an exposed nerve). The steady burning sensation is increased significantly by any light touch. Patients are somewhat numb in the areas affected by this burning pain. The burning and loss of touch appreciation are usually most severe on the distant parts of the body, such as the feet or hands. Pain may be moderate to severe in intensity and is often exacerbated by movement and temperature changes, usually cold temperatures.

Central pain syndrome may develop months or even years after injury or damage to the CNS. The disorder occurs in patients who have, or have had, strokes, multiple sclerosis, limb amputations, or brain or spinal cord injuries.

Generally pain medications provide little or no relief for those affected by central pain syndrome. Patients should be sedated and the nervous system should be kept quiet and as free from stress as possible. Central pain syndrome is not a fatal disorder. But for the majority of patients, the syndrome causes intractable pain.

The best way to manage pain is to treat its cause. For example, whenever possible, the cause of pain from cancer is treated by removing the tumor or decreasing its size. To do this, the doctor may recommend surgery, radiation therapy, or chemotherapy. When none of these procedures can be done, or when the cause of the pain is not known, pain-relief methods are used.

In the past, analgesics were differentiated as peripheral (e.g., aspirin, acetaminophen) and central acting (opioids) analgesics. Due to current better understanding of pain relief and analgesics, it is now more accepted to distinguish between non-opioid and opioid analgesics.

Non-opioid analgesics are often effective for mild to moderate pain and in treating pain arising from rheumatoid arthritis. Typical non-opioid analgesics are aspirin, acetaminophen and other nonsteroid anti-inflammatory drugs (NSAIDs), e.g., ibuprofen, piroxicam, and naproxen.

Opioid (or opiate) is a general term for natural or synthetic substances that bind to specific opioid receptors in the central nervous system producing an agonist action. Opioid analgesics are extremely useful in managing severe acute pain, postoperative pain and chronic pain including cancer pain. Typical opioid analgesics are codeine, morphine, methadone and fentanyl.

Traditional cancer pain relief methods include use of opiates such as codeine, hydromorphone (Dilaudid), levorphanol (Levo-Dromoran), methadone (Dolophine), morphine, oxycodone (in Percodan), and oxymorphone (Numorphan). They may be taken by mouth (orally, or PO), by injection (intramuscularly, or IM), through a vein (intravenously, or IV), or by rectal suppository. There are also other methods of giving pain medicines for more continuous pain relief. Not all narcotics are available in each of these forms.

NSAIDs similar to ibuprofen (in large doses, ibuprofen requires a prescription) are used for treatment of pain from cancer. Included in this group of pain relievers are Motrin, Naprosyn, Nalfon, and Trilisate. They are useful for moderate to severe pain. They may be especially helpful in treating the pain of bone metastasis.

It is believed that tetrodotoxin is not an opioid agonist since it does not bind specific opioid receptors in the CNS (central nervous system) producing an agonist action. Tetrodotoxin is a specific sodium channel blocker. Sodium channel blockers are used as local anesthetics, e.g., lidocaine. It is evident that tetrodotoxin is not an opioid agonist and therefore it could be assigned to the class of the non-opioid analgesics. As a result, tetrodotoxin has the potential to be a very strong non-opioid without a risk for addiction.

The inventors have discovered that tetrodotoxin (TTX), its analogs and derivatives are effective on pains produced by cancers such as liver cancer, rectal cancer, leiomyosarcoma, bone cancer, stomach cancer, lymphatic cancer, esophageal cancer and other major cancer types. Tetrodotoxin and its analogs and derivatives are effective in relieving pain in humans and other mammals resulting from malignant neoplasm (cancers) or other tumors. These cancers can occur in the genital organs (including prostate), digestive system (including stomach, colon), breast, respiratory system (including lung and bronchus), urinary system, lymphoma and skin cancer.

A person who has had an arm or leg removed by surgery may still feel pain or other unpleasant sensations as if they were coming from the absent limb. Doctors are not sure why it occurs, but phantom limb pain is real; it is not imaginary. This also can occur if a patient had a breast removed, resulting in a sensation of pain in the missing breast.

No single pain relief method controls phantom limb pain in all patients all the time. Many methods have been used to treat this type of pain, including pain medicine, physical therapy, and nerve stimulation. Tetrodotoxin administered in accordance with the method of the invention provides relief from the pain associated with phantom limb pain.

Since tetrodotoxin has high physiological activity, strong toxicity and a low safety threshold value, it is necessary to accurately and precisely control the formulation and dosage. Several methods reported in the literature for the determination of tetrodotoxin include biological measurement, UV spectrophotometry, fluorometry, gas chromatography, liquid chromatography, etc. All the techniques have their advantages and limitations. The biological measurement method is very sensitive and considered a feasible technique, however, it also has shortcomings like poor reproducibility, many influential factors, large variance between test animals, and deficiency of objectivity. TLC has relatively large sampling amount (20 $\mu$g) and low detection limit. The fluorometry method requires a fluorescence spectrophotometer. UV spectrophotometry cannot separate tetrodotoxin from related impurities, and its accuracy is poor. GC and the electrophoresis method also have their limitations, respectively.

Since it provides high specificity, high sensitivity, and is capable of providing identification and content determinations simultaneously, HPLC is used as the major detection method for content determination. By routine experimentation known to the skilled practitioner, the stationary phase, mobile phases and the detection conditions are optimized to establish a reliable separation and detection method. As a result, tetrodotoxin and the major related substances can be well separated. HPLC methods provide high detection sensitivity, convenience of operation, and sound reproducibility.

Tetrodotoxin useful in the method of the present invention can be obtained from animal tissues, such as puffer fish organs.

A detailed description of a method for production of tetrodotoxin and derivatives thereof is provided in Chinese application no. 00124516.3, filed Sep. 18, 2000.

The typical analogs of TTX possess only ⅛ to ⅟₄₀ toxicity of TTX, based upon bioassay in mice. It has been observed that the analogs produce joint analgesic action, and do not interact adversely.

The invention pertains to all sodium channel blocking compounds such as tetrodotoxin and saxitoxin. Chiriquitoxin (CTX) can be used. Also effective are analogs of tetrodotoxin such as 4-epi-tetrodotoxin, and anhydro-4-epi-tetrodotoxin.

Tetrodotoxin or TTX refers to the amino perhydroquinazoline compound having the molecular formula $C_{11}H_{17}N_3O_8$ and to derivatives thereof, including but not limited to anhydrotetrodotoxin, tetrodaminotoxin, methoxytetrodotoxin, ethoxytetrodotoxin, deoxytetrodotoxin and tetrodonic acid. Examples of TTX analogs include novel TTX analogs isolated from other organisms, as well as those that are partially or totally chemically synthesized. See e.g., Yotsu, M. et al. Agric. Biol. Chem., 53(3):893–895 (1989). Such analogs bind to the same site on the alpha subunit of sodium channels as does TTX.

Saxitoxin or STX refers to a compound comprising a tetrahydropurine moiety composed of two guanidine units fused together in a stable azaketal linkage, having a molecular formula $C_{10}H_{17}N_7O_2$, (mol. wt. 299.30) and to derivatives thereof, including but not limited to hydroxysaxitoxins and neosaxitoxin. Bower et al., Nonprotein Neurotoxins, Clin. Toxicol. 18(7): 813–863 (1981).

Preferred compounds for use in the invention are tetrodotoxin, 4-epi-tetrodotoxin, and anhydro-4-epi-tetrodotoxin.

Routes of administration of tetrodotoxin can include intramuscular injection, intravenous injection, subcutaneous injection, sublingual, patch through the skin, oral ingestion, implantable osmotic pump, collagen implants, aerosols or suppository. The routes of administration, the dosage and the administration schedule are shown in Table 1.

TABLE 1

Administration of Tetrodotoxin.

| Route of Administration | Dose ($\mu$g/50 kg subject) | Schedule |
| --- | --- | --- |
| Intramuscular injection | 5–50 | 4 ~ 2/day |
| Intravenous injection | 5–30 | 3 ~ 2/day |
| Subcutaneous injection | 5–50 | 4 ~ 2/day |
| Sublingual | 5–30 | 3 ~ 2/day |
| Patch through skin | 5–60 | 4 ~ 2/day |
| Oral ingestion | 5–30 | 3 ~ 2/day |
| Implantable Osmotic pump | 30–60 | 1 |
| Collagen implants | 30–60 | 1 |
| Aerosol | 5–50 | 4 ~ 2/day |
| Suppository | 5–30 | 3 ~ 2/day |

Typically, the active ingredient tetrodotoxin or saxitoxin is formulated into purified water or an acetic acid-sodium acetate buffer as a vehicle. However, the formulation can contain other components, including, but not restricted to, buffering means to maintain or adjust pH, such as acetate buffers, citrate buffers, phosphate buffers and borate buffers; viscosity increasing agents such as polyvinyl alcohol, celluloses, such as hydroxypropyl methyl cellulose and carbomer; preservatives, such as benzalkonium chloride, chlorobutanol, phenylmercuric acetate and phenyl mercuric nitrate; tonicity adjusters, such as sodium chloride, mannitol and glycerine; and penetration enhancers, such as glycols, oleic acid, alkyl amines and the like. The addition of a vasoconstrictor to the formulation is also possible. Combination formulations including the long-acting sodium channel blocking compound and an antibiotic, a steroidal or a non-steroidal anti-inflammatory drug and/or a vasoconstrictor are also possible.

Formulation for each administration route in Table 1 is generally considered known in the art. See, e.g., "Remington, the Science and Practice of Pharmacy", 19$^{th}$ ed., A. R. Gennaro, ed., c. 1995 by The Philadelphia College of Pharmacy and Science, (especially Part 7). As shown in Table 1, the typical dose ranges from 5 to 60 $\mu$g per adult. A more typical dose is from 20 to 40 $\mu$g per adult.

Tetrodotoxin, its analogs and derivatives are effective in relieving pain in humans and other mammals resulting from malignant neoplasm (cancers) or other tumors. These cancers can occur in the genital organs (including prostate), digestive system (including stomach, colon), breast, respiratory system (including lung and bronchus), urinary system, lymphoma and skin cancer, as shown in the following examples.

Sodium channel blockers are surprisingly shown to be effective as long-term systemic analgesics for alleviation of severe pain. It is also surprising that minimal side effects, the principal one being numbness in the lips and extremities, are observed upon systemic administration. Patients debilitated by pain are able to resume almost normal lives for periods of more than 20 days following a single course of treatment with TTX. That TTX and other sodium channel blockers can be used as systemic analgesics that are more effective than morphine and other opioid analgesics in treating acute, central and chronic pain is entirely unexpected.

An amount of a compound "effective for relieving pain" is an amount that results in a decrease in a patient's perception of pain by 2 units or more on the Numerical Pain Intensity Scale. An amount that is "very effective for relieving pain" is an amount that results in a decrease in a patient's perception of pain by 4 units or more on the Numerical Pain Intensity Scale. An amount of a compound "effective for eliminating pain" is an amount that results in a decrease in a patient's perception of pain to zero on the Numerical Pain Intensity Scale.

REFERENCES

1. Ran H P, Bevan S J, Dray A. Nociceptive peripheral neurones: cellular properties. In: Wall P D, Melzack R., editors. Textbook of pain, Edinburgh, chruchill livingstane, 1994; 57–78.
2. Woolf C J, Doubell T P. The pathophysiology of chronic pain-increased sensitivity to low threshold A β-fibre inputs. Current opinion in Neurobiology 1994; 4:525–534.
3. Dray A. Tasting the inflammatory soup: the role of peripheral neurones. Pain Reviews. 1994; 1:153–173.
4. Rabert D K, Koch B D, Ilnicka M, et al. A tetrodotoxin-resistant voltage-gated sodium channel from human dorsal root ganglia, hPH3/SCN 10A. Pain 1998; 78:107–114.
5. Catterall W A, Cellular and molecular biology of voltage-gated sodium channels, Physiol Rev. 1992; 72:s15–s18.
6. Akopian A N, Sivilotti L, Wood J N. A tetrodotoxin-resistant voltage-gated sodium channel expressed by sensory neurons, Nature, 1996; 379:257–262.
7. Gold M S, Reichling D B, Shuster M J, Levine J D. Hyperalgesic agents increase a tetrodotoxin-resistant Na+ current in nociceptors. Prod. Natl Acad Sci. USA, 1996; 93:1108–1112.
8. Khasar S G, Gold M S, Levine J D, A tetrodotoxin-resistant sodium current mediates inflammatory pain in the rat, Neuroscience letters, 1998; 256:17–20.
9. Novakovic S D, Tzoumaka E, McGivern J G, et al. Distribution of the tetrodotoxin-resistant sodium channel PN3 in rat sensory neurons in normal and neuropathic conditions, J. Neuroscience, 1998: 18:2174–2187.
10. Omana-zapata I, Khabbaz M A, Hunter J C, et al. Tetrodotoxin inhibits neuropathil ectopic activity in neuromas, dorsal root ganglia and dorsal horn neurons, Pain, 1997; 72:41–49.

EXAMPLES

Example 1

Formulation

The formulated pharmaceutical used in the clinical study of Example 2 is tetrodotoxin for injection. The formulation is shown in Table 2.

TABLE 2

| Tetrodotoxin formulation | |
| --- | --- |
| Tetrodotoxin | 15 mg |
| 0.5% dilute acetic acid | 1 ml |
| Acetic acid - acetate buffer solution | 50 ml (5% of the total volume of the prepared |

TABLE 2-continued

| Tetrodotoxin formulation | |
| --- | --- |
| (pH = 3.5) | pharmeceutical solution) |
| Water for injection□ add to | 1000 ml |

The calculation of the formulation dosage of TTX for injection is based upon the results of pre-clinical pharmacology and pharmacodynamics studies. The calculation of the clinical pharmaceutical dosage is based upon the dosage effective in animals. In general, it is calculated as ⅕ of the effective animal dosage. 50, 60, and 70 kg are used as human body weights, respectively.

The TTX analgesic $ID_{50}$ (half inhibition dosage) in the acetic acid-induced twisting test in mice is 2.80 μg/kg (intramuscularly, IM). Accordingly, the recommended clinical dosage for humans is:

$$2.80 \text{ μg/kg} \times (1/5) \times 50 \text{ (60, 70) kg} = 28.0 \text{ (33.6, 39.2) μg}$$

The TTX effective dosage in the formalin-induced inflammation test in rats is 2.5 μg/mg (IM) (P<0.01). Accordingly, the recommended clinical dosage for humans is:

$$2.50 \text{ μg/kg} \times (1/5) \times 50 \text{ (60, 70) kg} = 25.0 \text{ (30.0, 35.0) μg}$$

It is also possible to calculate the initial clinical dosage based upon $LD_{50}$ value. Considering the results of pharmacodynamics studies, the clinical dosage can be calculated as 1/50 of the $LD_{50}$. 50, 60, and 70 kg are used as human body weights, respectively.

Based upon the results of pharmacology studies and related references, the dosage of TTX for injection used in the clinical study of Example 2 is 30 μg in 2 ml.

Example 2

Clinical Study

A clinical study was carried out from Sep. 21 to Oct. 10, 1999 to examine the analgesic effect of tetrodotoxin injection (TTX purity 89%, brand name TETRODIN, batch no. 990122, Nanning Maple Leaf Pharmaceutical Co., Ltd., Guangxi, China) on 11 people who had chronic pain from advanced cancer.

1.1 Objects of Study

Eleven late term cancer patients volunteered to participate in this study. Computerized tomography (CT)-scans and pathological examination confirmed that all the patients had cancer. They all had moderate or severe pain according to the WHO endorsed criteria on "pain grading".

Among the 11 patients 6 were male, 5 were female. The oldest was 76, and the youngest 26. Five had liver cancer in late stage. One patient had leiomyosarcoma (smooth muscle sarcoma) accompanied by postoperative liver cancer. Two were postoperative relapse of stomach cancer. One was postoperative relapse of carcinoma of the esophagus. One was postoperative relapse of rectal cancer. One was colon carcinoma accompanied by liver cancer. All the patients joined this clinical trial voluntarily.

1.2 Drug and Dosage

Tetrodotoxin injection i.m., 30 μg/2 ml. All the patients were intramuscularly injected with 30 μg tetrodotoxin each time, twice a day (once every 12 hours). This was applied for 3 days (a total of 180 μg of tetrodotoxin).

1.3 Criteria of Evaluation

Following the clinical evaluation method as described below, the analgesic effect of tetrodotoxin on 11 people was determined. This study did not have a design control group; it was an open trial where both patients and doctors know what drug was being used.

Classification of Pain Intensity and Recording Method

The protocol required that no other analgesic drugs be taken for 24 hours before participating in the study. Nor were any other analgesic drugs taken during the 3-day period of the use of tetrodotoxin. Pain was evaluated using the Numeric Pain Intensity Scale, which is described below. Pain was initially evaluated prior to the initial tetrodotoxin injection. After each administration of tetrodotoxin (at 8:00 AM and 8:00 PM each day), a research staff member observed and recorded the pain intensity of every patient at the following 14 time intervals: 5 min, 10 min, 15 min, 20 min, 30 min, 1 h, 2 h, 3 h, 4 h, 5 h, 6 h 7 h, 8 h, and 12 h.

2.1 Recording the Method of Pain Intensity

For this test the WHO recommended method of 0~10 Numeric Pain Intensity Scale was used to calculate and record the pain intensity of the people in this test. Briefly, patients would self-evaluate their pain based upon a 0 to 10 numeric scale as shown below and then report it to a research assistant.

| 0 | 1 | 2 | 3 | 4 | 5 | 6 | 7 | 8 | 9 | 10 |
|---|---|---|---|---|---|---|---|---|---|---|

0=no pain; 1–4=mild pain; 5–6=moderate pain; 7–10=severe pain

Determination of Analgesic Effect 3.1 Pain Intensity Difference (PID)

PID is calculated by taking the pain intensity number before administration, and subtracting the pain intensity number at every time point after administration.

3.2 Pain Relief

After calculating the patient's pain intensity at each time interval, the researcher assesses the pain relief and assigns a value from one of the following five choices.

0: no relief

I: mild relief (the pain abates about 25%)

II: moderate relief (the pain abates about 50%)

III: significant relief (the pain abates about 75%)

IV: complete relief (the pain disappears completely)

3.3 Evaluating "Quality of Life"

Pain affects every patient's normal life and ability to continue with their everyday routine. This is generally referred to as their quality of life. Depending on the severity of the pain that is being experienced by each individual it can cause patients to experience irritability, depression and poor appetite. The researcher must consider any changes in the patient's quality of life, in the evaluation of the analgesic effect of any new drug. The numeric scale in the line below expresses the high and low reference numbers. It should be noted that this "quality of life" evaluation is a subjective issue and that the research doctor relies on the patient's descriptions of any changes (before and after administration of tetrodotoxin) in their quality of life as the primary means of input for making this evaluation. Issues that are questioned in regard to the quality of life include, routine daily activity, emotions, mobility (walking ability), normal work (includes both work outside the home and housework), sleeping state or pattern, relations with other persons, enjoyment of life.

Quality of life was evaluated by subjects themselves before and every 8 hours after administration.

The quality of life includes mood, walking ability, normal work (includes both work outside the home and housework), and relations with other people, sleep, and enjoyment of life. The numeric scale in the line below expressed the interfere extent of quality of life.

0: Does not interfere

1~3: Mildly interferes

4~7: Moderately interferes

8~9: Severely interfere

10: Completely interfere

| 0 | 1 | 2 | 3 | 4 | 5 | 6 | 7 | 8 | 9 | 10 |
|---|---|---|---|---|---|---|---|---|---|---|
| Does not interfere | | | | | | | | | | Pain completely interferes |

4. Results 4.1 Analgesic Effect

All subjects experienced various degrees of pain relief within 30 min. after the first administration of tetrodotoxin. Some of them reported noticeable pain relief in 5 min. After 3 days of the twice daily administration of tetrodotoxin, the pain intensity of all subjects was reduced to 0 in all but one patient who recorded a 1.

The results demonstrate that all of the patients, were totally relieved of their pain for between 20–30 days after the final administration of tetrodotoxin on the 3rd day. None of the patient's showed the slightest signs of having any symptoms of addiction following the three days of tetrodotoxin administration.

4.2 Effect on Daily Quality of Life

The patients reported that their "quality of life" was affected negatively, either moderately or severely by the pain caused by their cancer and/or their cancer treatment and medication. During the three day tetrodotoxin treatment and for the following 20~30 days, their quality of life showed distinct and dramatic improvements that were described, for example as severe interference that was reduced to moderate or mild interference. After 3 days of administration of tetrodotoxin, most of the patients could return to a normal life. Some of them returned to playing the popular game mahjong (a type of Chinese playing cards) with healthy people. They were able to go to the public bathhouse to bathe, an activity that had become to difficult to do due to the pain and anguish caused by the cancer. One of them took a long journey from Harbin to Beijing by train.

4.3 Side Effects

10–20 min after administration, all the patients felt numbness or tingling in their lips, tip of the tongue, ends of fingers and toes. These symptoms lasted at most about 30 min., then disappeared without any treatment. Two patients who had a long history of using dolantin experienced mild to moderate nausea accompanied by mild vomiting after only the first injection of tetrodotoxin. On the second injection, these symptoms did not appear. Some of the patients' blood pressure decreased 10–15 mm Hg, which recovered to normal 40–50 min later without any treatment. One of patients (after the first injection only) showed tachycardia with vomiting, this also disappeared 10–15 minutes later, without needing any treatment.

5. Conclusions

The following is observed when comparing tetrodotoxin to other analgesic drugs.

5.1 Less frequent administration of tetrodotoxin is required. The patient only needs one injection of 30 μg every 12 hours for up to 3 days. With these patients, the three-day administration of tetrodotoxin was immediately effective in reducing or eliminating their pain.

5.2 The short course of treatment of tetrodotoxin of only 3 days, as compared to any other strong analgesic that must be administered consistently and continuously to be effective, demonstrates that tetrodotoxin has considerable advantages over any other of the currently used analgesics.

5.3 Rapid effect. Tetrodotoxin takes effect at 5–30 min after administration.

5.4 Analgesic effect lasts longer. After 3 days of the twice daily administration of tetrodotoxin, the analgesic effect lasted 20–30 days. No patient reported the reappearance of pain in the period from the fourth to the twentieth day. In most instances the pain relief was effective for the entire 30 day monitoring period.

5.5 No signs of addiction or withdrawal occurred during or after treatment with tetrodotoxin. All of the other currently used narcotic analgesics are highly addictive and have untoward side effects.

5.6 Slight side effects. The subjects had only slight side effects, such as low blood pressure, nausea and vomiting. All of the side effects disappeared without any treatment within 15 to 60 minutes.

5.7 Tetrodotoxin also produced evident detoxification in the patients who were dependent on dolantin.

5.8 Tetrodotoxin improves the condition of cancer patients during their treatment. Tetrodotoxin does not have any direct effect on any of the cancers themselves. However, it was observed that the overall health and mental attitude of the patients improved substantially as they were relieved of the pain from their cancer.

Individual Case Results

Case 1

Mr. Gao, is a 44 year old male. He developed abdominal pain and was diagnosed with smooth muscle pain in the back wall of his celiac for which he underwent a surgical procedure. One year later, his abdomen pain relapsed and he was operated on again. The pathological examination from the second operation revealed that he had developed a smooth muscle sarcoma (leiomyosarcoma), later finding that his sarcoma had spread to his liver and that he now required and received anti-cancer treatment (chemotherapy). He began to inject Dolantin, because he could not bear the severe pain in his abdomen. He needed to inject Dolantin at least 3 times per day. Initially he was taking the Dolantin by intramuscular injection, and finally he needed to use intravenous injection in order to have the Dolantin take effect faster. Just prior to when he received the tetrodotoxin treatment, he had taken over 100 injections of Dolantin in the previous month. At the beginning, when he stopped using Dolantin, he experienced morphine-like withdrawal symptoms, such as whole body weakness and pain, trembling when standing up and difficulty walking. He voluntarily received tetrodotoxin treatment. His pain intensity scale was 8 before using tetrodotoxin. 5 minutes after the first injection of tetrodotoxin, his pain intensity on the 0 to 10 scale decreased to 0. After 3 days of treatment, he was able to go to the public bathhouse to bathe by himself. He went to a friend's home to play mahjong. To the date of this report, he is living normally and continues to feel comfortable without any pain.

Case 2

Mr. Zhang, is a 26 year old male. He felt pain in his liver area and was diagnosed with advanced liver cancer. His illness progressed to where he could not bear the severe abdominal pain and abdominal distention. He began to use Dolantin and other painkillers to relieve his pain. He volunteered to receive tetrodotoxin treatment. Before the first administration of tetrodotoxin, his pain intensity on the 0 to 10 scale was 8. On the second day of injecting tetrodotoxin, his pain intensity was reduced to 0. His life quality was also improved significantly. After completing 3-day's treatment, he traveled by train from Harbin to Beijing for further treatment of his cancer.

Case 3

Ms. Xie is a 76 year old female. She was diagnosed with rectal cancer and underwent surgery in 1996. In 1998, her rectal cancer spread to her liver. Her pain increased to where she was having difficulty dealing with the pain. She voluntarily received tetrodotoxin treatment. Her pain, intensity scale was reduced to 0 from 6, within 20 minutes after the first injection of tetrodotoxin. Her quality of life score also decreased to 6 from 10 after the first injection of tetrodotoxin. At the end of the 3 days of treatment with tetrodotoxin, she recovered to what she considered to be her normal life-style.

Case 4

Mr. Jin is a 63 year old male. He suffered from liver cancer for 8 years. In the last 6 months, his pain had escalated to where he could not be relieved of his pain by the use of other painkillers. He volunteered to receive the tetrodotoxin treatment. His pain intensity scale decreased to 0 from 7 on the second day of the tetrodotoxin treatment. His quality of life was also improved significantly.

Case 5

Ms. Duang, a 46 years old female, was diagnosed with lumbago, after which the symptoms associated with the lumbago gradually worsened. Painkillers were effective for managing the pain from her lumbago. Six months prior to this test, she started to experience pain in her left leg that became more and more severe. She was prescribed the progressively stronger painkillers, Tramadol, Pentazocine and Dolantin during this six months. During this same six months she was diagnosed with cancer that was initially of the liver, and had metastasized to bone cancer. The bone cancer was located in the $L_3$, $L_4$ and $T_{11}$ vertebrae and was evidenced by the presence of osteolytic lesions. Ms Duang volunteered to receive tetrodotoxin treatment. Immediately prior to starting the tetrodotoxin treatment, her pain intensity on the 0 to 10 scale was 9. Ten minutes after her first injection of tetrodotoxin, her pain intensity decreased to 7, and 20 minutes after her first injection, her pain intensity decreased to 2. At the conclusion of the 3 days treatment with tetrodotoxin her pain was entirely eliminated.

Case 6

Ms. Li is a 72 year old female who was experiencing abdominal distension and poor appetite. When an initial treatment did not take effect, an ultrasonic examination of her abdomen was done and she was diagnosed to have cancer of the liver. Her cancer appeared to be relieved after treatment by chemotherapy, but her abdominal distension and abdominal pain became worse. By the start of the test use of tetrodotoxin the painkillers that she was using could not relieve her pain. She volunteered to receive tetrodotoxin treatment in an attempt to reduce her pain. Before the administration of tetrodotoxin, her pain intensity on the 0 to 10 scale was 7. Ten minutes after she received her first of tetrodotoxin, her pain intensity scale was reduced to 0. After 3 days of treatment with tetrodotoxin, she was able to carry on with her life as if she had recovered back to normal.

Case 7

Mr. Li is a 36 year old male, who was diagnosed with advanced liver cancer. The pain in the region of his liver had increased to where he was not relieved of his pain by intramuscular injections of Dolantin. He volunteered to receive tetrodotoxin treatment. Previous to the administration of tetrodotoxin, his pain intensity on the 0 to 10 scale was 7. Twenty minutes after the first injection of tetrodotoxin, his pain intensity was reduced to 3. After the third injection of tetrodotoxin his pain intensity stabilized at 0. After 3 days of treatment his quality of life had improved significantly, achieving 0 interference.

Case 8

Mr. Cheng is a 60 year old male. He was diagnosed with mucinous adreno-carcinoma of the stomach and received surgery to remove the cancer. Three months after the operation, his abdomen became distended and he started to experience severe abdominal pain. A CTscan showed that the cancer had further extensively spread to his lungs, liver, abdominal cavity and lymph nodes. He volunteered to receive tetrodotoxin treatment. Prior to the first administration of tetrodotoxin, his pain intensity on the 0 to 10 scale was 8. Twenty min after injecting tetrodotoxin his pain intensity scale reduced to 0. After 3 days treatment he recovered to what he considered a normal life.

Case 9

Mr. Shi is a 59 year old male. He was diagnosed with carcinoma of the esophagus after one year of consistent retro-sterna pain that eventually became dysphagia. This was so severe in the last month that it was causing him to vomit after eating. After having surgery to remove the cancer, his pain was severe and was not relieved from the regular injections of Dolantin that he was prescribed. He volunteered to receive tetrodotoxin treatment. Prior to his first administration of tetrodotoxin, his pain intensity on the 0 to 10 scale was 8. After the second injection of tetrodotoxin, his pain intensity was reduced to 0. Following the 3 days of tetrodotoxin treatment he had recovered to what he considered a normal life.

Case 10

Ms. Liu is a 69 year old female who, three years after her operation to remove stomach cancer, found that the lymph node of her left cervical was swelling. A pathological examination showed that her stomach cancer had spread to the lymph node. For some time before she volunteered to receive tetrodotoxin treatment, her pain had increased to where she had difficulty dealing with it. Before the first administration of tetrodotoxin, her pain intensity on the 0 to 10 scale was 9. Three hours after the first injection of tetrodotoxin, her pain intensity scale reduced to 2, and after 3 days of treatment with tetrodotoxin, her pain intensity scale stabilized at 0.

Case 11

Ms. Tan is a 52 year old female whose rectal cancer relapsed one year after she had undergone surgery. The lump in her perineum was abscessed. The regional pain was extreme and was accompanied by headaches and dizziness at times so severe that she could not speak. She volunteered to receive tetrodotoxin treatment. Before the first administration of tetrodotoxin her pain intensity on the 0 to 10 scale was 7. One hour after the first injection of tetrodotoxin, her pain intensity was reduced to 0. At the completion of 3 days of treatment with tetrodotoxin she recovered to what she considered a normal life.

The results for the typical cases are summarized in Table 3.

TABLE 3

Summary of Tetrodotoxin Treating Cancer Pain

| No. | Name | Sex | Age | Disease Progress | Type of Pain | Dosage ($\mu$g) | Pain Rate Before Treatment | Pain Rate after treatment | Side Effect(s) |
| --- | --- | --- | --- | --- | --- | --- | --- | --- | --- |
| 1 | Gao HM | M | 44 | Smooth muscle sarcoma, spread to liver | Local pain, whole body pain | 180 | 8 | 0 | Numbness, nausea, vomit |
| 2 | Zhang BL | M | 26 | Late liver cancer | Colicky pain, swelling pain | 180 | 6 | 0 | Numbness |
| 3 | Xie SHQ | F | 76 | Rectal cancer, spread to liver | Dull pain, Local pain, whole body pain | 180 | 6 | 0 | Numbness |
| 4 | Jin DX | M | 63 | Liver cancer | Local pain, dull pain | 180 | 7 | 0 | Numbness |
| 5 | Duan YQ | F | 46 | Liver cancer, spread to bone | Stabbing pain | 180 | 9 | 1 | Numbness |
| 6 | Li SHQ | F | 72 | Liver cancer | Colicky pain, swelling pain | 180 | 7 | 0 | Numbness |
| 7 | Li BF | M | 36 | Late liver cancer | Colicky pain, swelling pain | 180 | 7 | 0 | Numbness |
| 8 | Cheng B | M | 60 | Stomach cancer | Local pain, dull pain | 180 | 8 | 0 | Numbness, nausea, vomit |
| 9 | Shi CHF | M | 59 | Postoperative relapse of carcinoma of esophagus | Local pain, dull pain | 180 | 8 | 0 | Numbness |
| 10 | Liu SM | F | 69 | Stomach cancer, lymphatic metastasis | Local pain, dull pain | 180 | 9 | 0 | Numbness |

TABLE 3-continued

Summary of Tetrodotoxin Treating Cancer Pain

| No. | Name | Sex | Age | Disease Progress | Type of Pain | Dosage (μg) | Pain Rate Before Treatment | Pain Rate after treatment | Side Effect(s) |
|---|---|---|---|---|---|---|---|---|---|
| 11 | Tan XCH | F | 52 | Postoperative relapse of rectal cancer | Local pain, dull pain | 180 | 7 | 0 | Numbness |

Example 3

Effects of TTX on Nociception in Rats and Mice

Test Materials

TTX, pure powder, batch no. 960510, supplied by Dalian Ao Sen Pharmaceutical Plant, Liaoning, China. It was diluted with distilled water to required concentrations, and the pH was adjusted with acetic acid to 4–5.

Glacial acetic acid, analytically pure, Beijing 52952 Chemical plant, Batch No. 910613.

Formalin 40%, superior purity, Beijing No.3 Chemical plant, Batch No. 950712.

Aspirin powder, purity 99%, Xinhua Pharmaceutical Factory, Batch No. 9205292.

Hydrochloric morphine, Qinhai Pharmaceutical Factory, Batch No. 960804.

Animals

Kunming mice, 18–22 g, supplied by the Animal Centre of the Chinese Academy of Medical Sciences. Quality certificate No.: Jing Dong Guan Zi (1994) 029.

Wistar rats, 180–240 g, half of each sex, supplied by the Experimental Animal Department, Beijing Medical University. Quality certificate No.: Jing Dong Guan Zi (1994) 092.

3.1 Acetic Acid-induced Writhing Test in Mice

Mice were randomly divided into TTX-tested groups, positive control groups (Aspirin and Meperidine) and negative control group (normal saline). The mice were fasted for 12 hours before the test, and allowed to drink water ad-libitum. TTX was given sc or im., and 40 minutes later, 0.6% acetic acid (0.1 ml/10 g) was given i.p. as a chemical stimulus. The writhing incidence in the mice were observed and recorded within the following 15 minutes. The mice in normal saline (NS) group, aspirin group and Meperidine group were treated the same way. The writhing incidences in the TTX groups were compared to the control group, and the following formula was used to calculate the inhibition rate of TTX on writhing:

Inhibition rate (%)=(the writhing incidence in the control group−that of the TTX group)/the writhing incidence in the control group×100%

The medium inhibition dose, $ID_{50}$, was calculated using the Logit method.

See Tables 4 and 5 for the results.

As shown in Tables 4 and 5, the analgesic potency of TTX is similar in different routes of administration. The analgesic effect of TTX was much stronger than that of aspirin, and was 670 times stronger than meperidine.

TABLE 4

The $ID_{50}$ values of TTX, aspirin and meperidine in mice writhing test (sc)

| Groups | Number of animals tested (n) | Writhing incidents (n) | Percentage of inhibition (%) | $ID_{50}$ and 95% Confidence Interval |
|---|---|---|---|---|
| NS | 20 | 16.7 | | |
| TTX (μg/kg) | | | | |
| 1.0 | 20 | 12.5 | 25.2 | 2.68 |
| 2.5 | 20 | 6.9 | 46.7 | (2.32 ~ 3.53) |
| 5.0 | 20 | 6.9 | 58.7 | μg/kg |
| 10.0 | 20 | 2.8 | 82.2 | |
| Aspirin (mg/kg) | | | | |
| 100 | 20 | 15.0 | 18.9 | 198.8 |
| 200 | 20 | 9.96 | 46.2 | (181.7 ~ 217.5) |
| 300 | 20 | 5.66 | 69.4 | mg/kg |
| 400 | 20 | 2.7 | 85.4 | |
| Meperidine (mg/kg) | | | | |
| 1.0 | 20 | 14.2 | 23.2 | 1.8 |
| 2.0 | 20 | 8.2 | 55.6 | (1.6 ~ 2.1) |
| 3.0 | 20 | 6.1 | 67.0 | mg/kg |
| 4.0 | 20 | 3.1 | 83.2 | |
| 5.0 | 20 | 0.31 | 98.3 | |

TABLE 5

The $ID_{50}$ values ot TTX, aspirin in mice writhing test (im)

| Group | Number of Animals | Average Writhing Incidents | Inhibition Rate % | $ID_{50}$ (95% Confidence Interval) |
|---|---|---|---|---|
| NS control | 20 | 28.2 | — | |
| TTX (μg/kg) | | | | |
| 1.25 | 20 | 20.9 | 25.9 | 2.80 |
| 2.50 | 20 | 15.7 | 43.9 | (2.37 ~ 3.26) |
| 5.00 | 20 | 9.4 | 66.7 | μg/kg |
| 10.00 | 20 | 3.2 | 88.7 | |
| Aspirin (mg/kg) | | | | |
| 100 | 20 | 22.1 | 21.7 | 183.8 |
| 200 | 20 | 14.3 | 49.3 | (164.9 ~ 202.4) |
| 300 | 20 | 7.2 | 74.4 | mg/kg |
| 400 | 20 | 2.7 | 90.6 | |

3.2 Formalin Induced Inflammation Test in Rats

Wistar rats were randomly divided into a TTX-tested group, positive control group (Morphine) and a negative control group (normal saline). The rats were fasted for 12 hours before the test, meanwhile allowed to drink water ad-libitum. 2.5% Formalin was used as the pain stimulus. TTX was injected i.m. or s.c. in the rats at different doses and then they were held in 20 cm×20 cm×20 cm clear plastic boxes for observation. Forty minutes later, 0.06 ml 2.5% Formalin was injected s.c. in the plantar surface of the right hind paw of rats. The pain responses of the rats, such as licking/gnawing, twitching, and lifting the right hind paw, were observed and recorded in the following 5 minutes. Pain response scores were calculated using the following formula:

Pain response score=licking/gnawing time (sec)×3+twitching occurrences×⅔+lifting time (sec).

The rats in the normal saline (NS) group and morphine group were treated similarly. The inhibition rate of TTX on pain responses was calculated by:

Inhibition rate (%)=(the average of the pain response scores of the control group−that of the TTX group)/the average of the pain response scores of the control group×100%.

The median inhibition dose, $ID_{50}$, is calculated by the Logit method.

See Tables 6 and 7.

TABLE 6

The $ID_{50}$ values (sc) of TTX and Morphine in Formalin test in rats

| Group | Number of animals | Scores of pain responses | Inhibition rate (%) | $ID_{50}$ (95% CI) |
|---|---|---|---|---|
| NS control | 8 | 237.5 | | |
| TTX (μg/kg) | | | | |
| 0.3 | 8 | 186.4 | 21.5 | 0.82 (0.66 ~ 1.00) |
| 0.6 | 8 | 132.9 | 44 | μg/kg |
| 1.25 | 8 | 72.1 | 69.6 | |
| 2.5 | 8 | 67.3 | 71.7 | |
| 5.0 | 8 | 41.3 | 82.6 | |
| Morphine (mg/kg) | | | | |
| 0.6 | 8 | 210.7 | 11.3 | 2.63 (2.32 ~ 2.98) |
| 1.25 | 8 | 190.7 | 19.7 | mg/kg |
| 2.5 | 8 | 158.2 | 33.4 | |
| 5.0 | 8 | 46.1 | 80.6 | |
| 10.0 | 8 | 13.1 | 94.2 | |

TABLE 7

The $ID_{50}$ values (im) of TTX and Morphine in Formalin test in rats

| Groups | Number of animals | Scores of pain responses | Inhibition rate (%) | $ID_{50}$ (95% CI) |
|---|---|---|---|---|
| NS | 20 | 203.6 | | |
| TTX (μg/kg) | | | | |
| 0.25 | 10 | 152.7 | 25.0 | 0.93 |
| 0.50 | 10 | 116.0 | 43.0 | (0.56 ~ 1.56) |
| 2.50 | 10 | 57.2 | 71.9 | μg/kg |
| 5.0 | 10 | 48.5 | 76.2 | |
| 10.0 | 10 | 45.9 | 77.5 | |

TABLE 7-continued

The $ID_{50}$ values (im) of TTX and Morphine in Formalin test in rats

| Groups | Number of animals | Scores of pain responses | Inhibition rate (%) | $ID_{50}$ (95% CI) |
|---|---|---|---|---|
| Morphine (mg/kg) | | | | |
| 2.5 | 10 | 131.2 | 35.6 | |
| 3.5 | 10 | 51.6 | 74.6 | 2.74 |
| 5.0 | 10 | 30.1 | 85.2 | (2.24 ~ 3.35) |
| 6.5 | 10 | 22.7 | 88.9 | mg/kg |
| 8.0 | 10 | 5.2 | 91.0 | |

As shown in Tables 6 and 7, TTX and morphine both had significant analgesic effects in the Formalin test, while TTX's analgesic effect was 3200–2900 times stronger than morphine by subcutaneous and intramuscular injection, respectively.

3.3 Tail-flick Tests in Rats

The analgesic effects of TTX and morphine on thermal-induced pain were studied by the tail-flick test in rats.

Rats were randomly divided into 7 groups, each consisting of 8 rats. The rats were fasted for 12 hours before testing, but allowed to drink water ad-libitum. A rat was immobilized on a tail-flick algometer, and then a loading electric voltage of 12 V was applied to a light bulb as a thermal stimulus to the tail end of the rat, and the tail-flick latency was recorded subsequently. If a rat did not respond within a period of 5–8 seconds, it would be rejected. The testing was performed after TTX was injected. If the pain threshold rose so high, such that the rat failed to flick its tail within 20 seconds of exposure to the stimulation, the illumination would be terminated to avoid blistering and damage to the skin. In such a case, the latency was considered to be 20 seconds.

The results showed that TTX, at dose levels of 1.25~5.0 μg/kg, produced pronounced analgesia effects on thermal induced pain in the tail-flick test in rats, but did not at lower dose levels of 0.3~0.6 μg/kg. These effects were less potent than morphine (see Table 8).

TABLE 8

Analgesia effects of TTX and morphine on thermal-induced pains in the tail-flick test in rats

| Group | Number of animals | Latency time (minutes) |
|---|---|---|
| Normal saline control | 8 | 7.6 ± 3.8 |
| TTX (μg/kg) | | |
| 0.3 | 8 | 8.3 ± 3.7* |
| 0.6 | 8 | 10.3 ± 4.9* |
| 1.25 | 8 | 13.9 ± 4.2** |
| 2.5 | 8 | 17.0 ± 3.5*** |
| 5.0 | 8 | 17.3 ± 3.8*** |
| Morphine (mg/kg) | | |
| 5.0 | 8 | >20 |

$\bar{X}$ ± SD
*$P > 0.05$
**$P < 0.05$
***$P < 0.01$, compared to the normal saline control group.

3.4 Study of Analgesic Time-effect Relation of TTX

The analgesic time-effect relation of TTX and aspirin was examined by administering TTX (sc or im) and aspirin (po)

at doses twice their $ID_{50}$ values, 6 μg/kg and 400 mg/kg, respectively, in acetic acid-induced writhing tests in mice. The results indicated that dosing TTX by different administration routes (im or sc) produced similar results. The onset of TTX's therapeutic effect was 15 minutes, reached a peak effect at 1 hour after dosing, and its analgesic effect lasted about 5 hours. Aspirin started therapeutic effect at 20 minutes, reached a peak effect at 30 minutes after dosing, and its analgesic effect lasted about 2 hours (see Tables 9, 10, 11, 12).

TABLE 9

The time-effect relation of TTX in the mouse writhing test (sc)
Time after dosing (minutes.)

|  | 15 | 30 | 60 | 120 | 180 | 240 | 300 | 330 |
|---|---|---|---|---|---|---|---|---|
| AWI[1] | 9.9 ± 9.4 | 8.7 ± 4.0 | 6.0 ± 5.5 | 16.9 ± 14.4 | 7.6 ± 11.7 | 18.5 ± 13.4 | 18.6 ± 11.1 | 22.8 ± 10.1 |
| IR[2] | 64.9 | 69.1 | 78.7 | 40.1 | 72.5 | 34.0 | 34.0 | 19.1 |
| P value | <0.01 | <0.01 | <0.01 | <0.05 | <0.01 | <0.05 | <0.05 | >0.05 |

AWI[1] Average writing incidence. Compared to the NS group, 28.2 ± 12.4.n = 20
IR[2] Inhibition rate %

TABLE 10

The time-effect relation of aspirin in the mouse writhing test (ig)
Time after dosing (minutes)

|  | 10 | 20 | 30 | 40 | 70 | 100 | 130 |
|---|---|---|---|---|---|---|---|
| AWI[1] | 11.4 ± 9.9 | 10.9 ± 10.1 | 1.98 ± 0.2 | 4.8 ± 1.1 | 6.3 ± 1.4 | 11.6 ± 2.5 | 11.8 ± 9.5 |
| IR[2] | 38.4 | 41.1 | 89.2 | 74.1 | 65.9 | 37.1 | 36.2 |
| P value | >0.05 | <0.05 | <0.01 | <0.01 | <0.01 | <0.05 | >0.05 |

Average writhing incidence of the NS group, 18.5 ± 6.4, n = 20

TABLE 11

The time-effect relation of TTX in the mouse writhing test (im)
Time after dosing (minutes)

|  | 15 | 30 | 60 | 120 | 180 | 240 | 300 | 360 |
|---|---|---|---|---|---|---|---|---|
| AWI[1] | 10.4 ± 8.2 | 8.0 ± 5.3 | 5.4 ± 4.1 | 15.7 ± 7.1 | 8.8 ± 6.1 | 10.5 ± 5.8 | 15.7 ± 5.0 | 22.3 ± 9.8 |
| IR[2] | 63.2 | 71.6 | 80.9 | 44.3 | 68.8 | 62.8 | 44.3 | 20.9 |
| P value | <0.01 | <0.01 | <0.01 | <0.05 | <0.01 | <0.01 | <0.05 | >0.05 |

Average writhing incidence of the NS group, 28.2 ± 14.3, n = 20

TABLE 12

The time-effect relation of aspirin in the mouse writhing test (ig)
Time after dosing (minutes)

|  | 10 | 20 | 30 | 45 | 60 | 90 | 120 | 150 |
|---|---|---|---|---|---|---|---|---|
| AWI[1] | 19.5 ± 11.7 | 17.7 ± 9.2 | 5.5 ± 1.2 | 8.2 ± 2.7 | 10.2 ± 3.6 | 14.4 ± 5.8 | 19.3 ± 3.1 | 22.8 ± 9.7 |
| IR[2] | 30.8 | 37.2 | 80.6 | 70.9 | 63.8 | 49.0 | 31.6 | 19.3 |
| P value | >0.05 | <0.05 | <0.01 | <0.01 | <0.01 | <0.01 | <0.05 | >0.05 |

Average writhing incidence of the NS group, 28.2 ± 14.3, n = 20

Example 4

Physical Dependence Study with TTX in Mice, Rats and Monkeys

The physical dependence potential of tetrodotoxin (TTX) was studied in three species of animals and four animal models. Kuiming mice, Wistar rats and Guangxi monkeys (sub-species of Rhesus monkey) were used in this study.

Body weight:
 Rats: 190–230 g/ea.
 Mice: 20–25 g/ea.
 Monkeys: 3–6 kg/ea.
Gender:
 Rats or mice: half male, half female.
 Monkeys: either sex.
Numbers of animals per group:
 Mice: 10/sex/group.
 Rat: 5/sex/group.
 Monkey: 3–6.
Volume administered per animal:
 Mice: 0.1 ml/per10 g body weight.
 Rat: 0.2 ml/100 g.
 Monkey: 0.1 ml/kg.
Material:
 Tetrodotoxin powder, batch no. 950314, supplied by Dalian Ao Sen Pharmaceutical Plant, Liaoning, China.

4.1 Precipitate Jumping Test in Mice

Mice were randomly divided into two TTX groups (5.5 μg/kg and 11.5 μg/kg), one morphine group (constantly dosing morphine 20 mg/kg) as a positive control, and one normal saline (equal volume of NS) group as a negative control. All those agents were given subcutaneously 3 times a day and dosed constantly for 7 days, respectively. At day 8, 10 mg/kg $M_{5050}$, a morphine receptor antagonist, was used to precipitate withdrawal at two hours after the last administration, then the jumping incidence and the jumping frequency were recorded. The results showed that data obtained for the morphine group were significantly different from those obtained for the TTX group and the NS control group, but no significant difference was observed between the TTX group and the NS control group. This indicates that, at the dose levels used in this study, TTX administered subcutaneously to mice for 1 week at a constant dosage yielded the same results as normal saline, as neither of them produced signs of physical dependence in mice (Table 13).

TABLE 13

Comparison of jumping results in mice administered
TTX, morphine and NS

| Group | No. of Mice (n) | Jumping Incidence (%) | Jumping Frequency (X ± SD) |
|---|---|---|---|
| Morphine | 20 | 90.0 | 19.7 ± 16.3 |
| NS | 10 | 20.0* | 0.80 ± 2.20* |
| TTX (high dosage) | 20 | 10.0*# | 0.70 ± 2.70* |
| TX (low dosage) | 20 | 10.0*# | 1.30 ± 3.90* |

Note:
*$P < 0.05$ compared with morphine
$P > 0.05$, compared with normal saline.

4.2 Precipitate Withdrawal Test in Rats

Rats were randomly divided into two TTX groups, one morphine group that was used as a positive control, and one normal saline (equal volume of NS) group as a negative control. The dosing schedule is following: TTX group dosages started from 1.5 μg/kg and 3.0 μg/kg, respectively. Dosages were progressively escalated to 9 and 12 μg/kg for day 7, respectively. The morphine group was given 5, 10, 15, 20, 25, 30 and 35 mg/kg, escalating the dose each day. Normal saline (equal volume of NS) was used as a negative control. All these doses were given subcutaneously 3 times a day. At day 8, 2 mg/kg $M_{5050}$ was used to precipitate withdrawal at 2 hours after the last administration, then the withdrawal reactions and body weight loss were monitored.

The results showed that the scores for withdrawal symptoms and body weight loss for both the TTX dose groups were similar to those for the NS group, but were markedly lower than the scores observed for the morphine group. The difference was found to be very significant ($p<0.01$). These results indicate that TTX did not produce a physical dependence response in rats when administered subcutaneously at the doses used in the test (Table 14).

TABLE 14

Comparison of precipitate withdrawal scores in
groups treated with TTX, morphine and NS.

| Group | Score of withdrawal symptoms (Mean ± SD) | Score of body weight loss (Mean ± SD) |
|---|---|---|
| Morphine | 7.38 ± 1.16 | 10.00 ± 2.60 |
| NS | 0.40 ± 1.20* | 0.00 ± 0.00* |
| TTX (high dosage) | 0.30 ± 0.90*# | 0.00 ± 0.00*# |
| TTX (low dosage) | 0.20 ± 0.60*# | 0.00 ± 0.00*# |

Note:
*$P < 0.01$ compared with morphine
$P > 0.05$ compared with normal saline 4.3 Precipitate Withdrawal Test in Monkey Monkeys were assigned to a morphine positive control group, a normal saline (NS) negative control group, and a TTX group, and each group was dosed three times a day (at 08:30, 14:30, and 20:30). A morphine dependence model was created by progressively escalating the dosage. The dosage of morphine was maintained at 3 mg/kg for three days, then escalated to 6 mg/kg for three days, 9 mg/kg for four days, and 12 mg/kg for four days, until it reached 15 mg/kg in week 3 and remained at that level until the one month mark. TTX was administered at dosages of 1, 2 and 3 μg/kg for one week each. When the dosage was increased to 4 μg/kg in week 4, a significant toxic reaction (vomiting) occurred, so the dosage was decreased back to 3 μg/kg. In all groups TTX was administered for one month. One hour after the final dose was administered at 8:30 a.m. on day 31, the monkeys were given a subcutaneous injection of 1 mg/kg of naloxone, and were then promptly observed within the next hour for withdrawal symptoms and for their percentage change in body weight.

The result indicated that the scores for withdrawal symptom and the percentages of body weight loss in the TTX and NS groups were markedly lower than those noted in the morphine group ($p<0.01$), and that both the scores of withdrawal symptom and the percentages of body weight loss were very similar between the TTX group and the NS group. This showed that the use of the morphine antagonist naloxone to precipitate withdrawal in the monkeys with long-term administration of TTX did not cause morphine-like withdrawal symptoms, i.e., TTX does not possess such characteristics as causing opiate physical dependence (Table 15).

TABLE 15

Results of precipitate withdrawal test in monkeys
treated with TTX, morphine and NS (Mean ± S.D.)

| Group | n | Score of Withdrawal Symptoms | Body Weight Loss (%) |
|---|---|---|---|
| Morphine | 3 | 61.0 ± 2.6 | 6.6 ± 1.7 |
| NS | 3 | 2.6 ± 4.6* | 0.7 ± 0.6* |
| TTX | 6 | 2.6 ± 4.6*# | 0.4 ± 0.8*# |

Note:
*$P < 0.01$ compared with morphine
$P > 0.05$ compared with normal saline 4.4 Natural Withdrawal Test in Monkeys Monkeys were assigned to a morphine positive control group, a NS negative control group, and a TTX group, and were dosed following the same steps and methods used in the precipitate withdrawal test. After 30 days, the high doses of the precipitate withdrawal test were continued until day 90, at which time the administration of morphine, TTX and NS was stopped. The withdrawal symptoms and body weight changes occurring in each group were then monitored during the week following the termination of treatment, with observations being made three times a day, and the findings were scored according to the observation tables (See Attachments 1, 2 and 3).

The results in Tables 16 and 17 showed that no withdrawal symptoms were observed for one week after the continuous administration of TTX for three months had ended. Within three days after administration was stopped, a few monkeys occasionally appeared somewhat excited and restless, but this behavior soon disappeared. The body weight of the TTX treated monkeys not only did not decline, but on the contrary, increased as compared to the weights noted during the administration period. The morphine control group, on the other hand, manifested obvious withdrawal symptoms. This indicates that the long-term administration of TTX does not produce any signs of physical dependence.

TABLE 16

Comparison of withdrawal symptom scores during the natural withdrawal period (Mean ± SD)

| | | No. of days after withdrawl | | | | | | |
|---|---|---|---|---|---|---|---|---|
| Group | n | 1 | 2 | 3 | 4 | 5 | 6 | 7 |
| Morphine | 4 | 34.8 ± 26.4 | 35.3 ± 20.5 | 28.3 ± 5.4 | 16.3 ± 7.5 | 15.3 ± 5.7 | 10.3 ± 0.5 | 10.5 ± 2.5 |
| TTX | 6 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 |
| NS | 3 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 |

15

TABLE 17

Percentage change in body weight in each group of monkeys during period of natural withdrawal (Mean ± SD)

| | | No. of Days After Withdrawal | | | | | | | Overall Mean |
|---|---|---|---|---|---|---|---|---|---|
| Group | n | 1 | 2 | 3 | 4 | 5 | 6 | 7 | X ± SD |
| Morphine | 4 | −4.8 ± 0.4 | −7.1 ± 2.5 | −5.4 ± 3.4 | −5.9 ± 2.0 | −6.8 ± 2.4 | −6.6 ± 2.4 | −5.9 ± 1.4 | −6.1 ± 0.8 |
| NS | 3 | 1.6 ± 2.9 | 2.4 ± 1.5 | 3.0 ± 0.8 | 3.1 ± 0.7 | 3.0 ± 1.8 | 2.4 ± 1.1 | 2.8 ± 2.6 | 2.6 ± 0.5* |
| TTX | 3 | 1.6 ± 1.4 | 2.9 ± 3.7 | 3.8 ± 2.9 | 3.1 ± 1.8 | 3.7 ± 2.7 | 3.5 ± 2.8 | 4.1 ± 1.6 | 3.2 ± 0.8*# |

Note:
*$P < 0.01$ compared with morphine
$P > 0.05$ compared with the NS groups Attachment 1:
Observation table for withdrawal symptoms in precipitate withdrawal test in rats.
Year    Month    Day

| Rat No. | Sex | Test Drug | Pre-withdrawal Body Weight (g) | | | | | |
|---|---|---|---|---|---|---|---|---|
| | Symptoms | | Scoring | 15' | 30' | 45' | 60' | 90' | 120' |
| Behaviors | Wet-dog shakes | | (2) | | | | | | |
| | Irritability on touch | Mild | (1) | | | | | | |
| | | Severe | (2) | | | | | | |
| | Teeth-chattering | Intermittent | (0.5) | | | | | | |
| | | Continuous | (1) | | | | | | |
| Autonomic Nervous System Symptoms | Lacrimation | | (4) | | | | | | |
| | Diarrhea | Soft stools | (4) | | | | | | |
| | | Unformed stools | (8) | | | | | | |
| | Salivation | Mild | (1) | | | | | | |
| | | Severe | (2) | | | | | | |
| Post-withdrawal body weight (g) | | | | | | | | | |
| Percentage of Body weight change | | | | | | | | | |

Note:
Total score:

| | | Attachment 2 | | | | | | | |
|---|---|---|---|---|---|---|---|---|---|
| | | Observation table for withdrawal symptoms in monkeys. | | | | | | | |
| No. | ♀ ♂ | Body weight (kg) | Time of final dosing | | | Month | Day | Hour | |
| | | On day | On day | | | On day | | | |
| Symptom | /Time | 8:00  14:30  20:30 | 8:00 | 14:30 | 20:30 | 8:00 | 14:30 | 20:30 | |
| Mild | Restlessness | | | | | | | | |
| | Irritability | | | | | | | | |
| | Crying | | | | | | | | |
| | Lack of appetite | | | | | | | | |
| | Loose stools | | | | | | | | |
| | Salivation | | | | | | | | |
| | Rhinorrhea | | | | | | | | |
| | Facial flushing | | | | | | | | |
| Moderate | Tremors | | | | | | | | |
| | Anorexia | | | | | | | | |
| | Muscular rigidity | | | | | | | | |
| | Twitching | | | | | | | | |
| | Piloerection | | | | | | | | |
| | Clasping of the abdomen | | | | | | | | |
| | Supination in weakness | | | | | | | | |
| Severe | Diarrhea | | | | | | | | |
| | Abnormal posture | | | | | | | | |
| | Vomiting | | | | | | | | |
| | Lateral decumbency with closed eyes | | | | | | | | |
| Very severe | Exhaustion State | | | | | | | | |
| | Death | | | | | | | | |
| Total symptom score | | | | | | | | | |
| Body weight (kg) | | | | | | | | | |
| Body temperature (° C.) | | | | | | | | | |

Attachment 3
Grading of Monkey Withdrawal Symptoms and Scoring Method
I. Grading
1. Mild: Fear, yawning, lacrimation, trembling, facial flushing, sweating, crying, irritability, reduced appetite, loose stools.
2. Moderate: Tremors, anorexia, piloerection, muscle twitch, clasping of the abdomen, diarrhea, and anergic supination.
3. Severe: Extreme restlessness, lateral recumbency with closed eyes, abnormal posture, vomiting, facial pallor, and conspicuous myospasms
4. Very severe: Exhaustion (blank expression, dyspnea, dehydration), pronounced body weight loss, circulatory failure, and death.

II. Scoring (Score of Grades Classification+Symptom Score)
Mild: 5 points for the grade classification, 3 points for each symptom, with 1 point being subtracted for a repeated manifestation of the same symptom within a given day.
Moderate: 10 points for the grade classification, 4 points for each symptom, with 1 point being subtracted for a repeated manifestation of the same symptom within a given day.
Severe: 17 points for the grade classification, 4 points for each symptom, with 1 point being subtracted for a repeated manifestation of the same symptom within a given day.
Very severe: 32 points for the grade classification, 20 points for exhaustion, 30 points for death.

III. Basis of Scoring
When there is a difference in the grading of a symptom, the scoring should be different. Moreover, the scoring should also vary depending on the number of symptoms within the same grade classification, but the resulting score should not be higher than warranted for the grade classification.

The score for three symptoms of a grade class equals the score for one symptom of the immediate higher-grade class. For example, three symptoms scored as being of mild severity (5+(3×3))=1 symptom scored as being of moderate severity (10+4).

Three symptoms scored as being of moderate severity (10+(4×3))=1 symptom scored as severe (17+5).

If the animal appears exhausted or dies, any other symptoms are ignored, so that the assigned score is equivalent to the sum total of the scores for mild, moderate and severe symptoms.

Example 5
General Pharmacological Studies of Tetrodotoxin
Test Materials
Tetrodotoxin powder, batch no. 971208, supplied by Dalian Ao Sen Pharmaceutical Plant, Liaoning, China. The drug was dissolved in normal saline at appropriate concentrations for intraperitoneal injection (0.1 ml per 10 g of body weight).

Caffeine: Shanghai Second Chemical Reagents Co, Batch No. 950801.

Diazepam injection solution: People's Pharmaceuticals of Tianjing Amino Acid Co., Batch No. 970424.

Morphine: National Institute on Drug and Biological Product, Batch No. 1201-9612. Sodium pentobarbital: Beijing Tongxian Yuchai Fine Chemicals, Batch No. 950427.

Animals
Kunming mice (17 g to 22 g), half male and half female, were used in the study. The differences of body weight between animals in each test were not larger than 5 g.

5.1 Effects on the General Behavior of Mice

Mice were randomly divided into 6 groups of 10 mice each. The animals were injected intraperitoneally with TTX (2.5, 5, and 10 μg/kg), Caffeine (10 mg/kg), Diazepam (5.0 mg/kg) or normal saline, respectively. Fifteen minutes after dosing, changes in general behavior, gesture, gait, presence of excessive salivation and muscular tremor, and change in the size of pupils were recorded.

The test results showed that after being given a single dose of 2.5 μg/kg or 5.0 μg/kg of TTX, the mice exhibited normal gestures and gaits, no excessive salivation or amyostasia, and no change in the size of pupils. Only the mice treated with a single dose of 10 μg/kg of TTX generally manifested eye-closing and reduced physical movements.

5.2 Effects on the Autonomic Mobility of Mice

Mice were randomly divided into 12 groups of 12 mice each, and were assigned to three TTX groups at doses of 2.5, 5.0, and 10 μg/kg, respectively, and two positive control groups, i.e. a caffeine 10 mg/kg group (central nervous system (CNS) stimulant), a diazepam (5mg/kg) group (CNS depressant), and a blank control group (normal saline). Testing was conducted on the TTX groups and the control groups, alternatively. Fifteen minutes after the administration, the mice (in groups of 4) were put into a TDW-02 general locomotive movement recorder and stabilized for five minutes. Then, for the following five minutes, the locomotive movements of the mice were recorded and the results among the TTX groups, the positive control groups and the blank control group were compared. Whether these differences were significant or not was determined using the t-test.

The test results showed that after being given a single dose of 2.5 μg/kg or 5.0 μg/kg of TTX, the mice exhibited normal gestures and gaits, no excessive salivation or amyostasia, and no change in the size of pupils. Only the mice treated with a single dose of 10 μg/kg of TTX generally manifested eye-closing and reduced physical movements.

Therefore their autonomic mobility was significantly lower than those of the blank control group ($P<0.01$) but not so when compared to the positive control (diazepam) group ($P>0.05$), suggesting TTX at this dose (10 μg/kg) has sedative effects to some extent (Table 18).

TABLE 18

Effects of Tetrodotoxin (TTX) on the autonomic mobility of mice

| Drugs | Dose level | Number of animals | Number of autonomic mobility ($\bar{X} \pm$ SD) |
|---|---|---|---|
| Normal saline | — | 12 | 591 ± 111 |
| Caffeine | 10 mg/kg | 12 | 777 ± 178 *** ••• |
| Diazepam | 5.0 mg/kg | 12 | 323 ± 203 *** ||| |
| TTX | 2.5 μg/kg | 12 | 547 ± 99 |||••• |
| TTX | 5.0 μg/kg | 12 | 540 ± 118 |||••• |
| TTX | 10 μg/kg | 12 | 442 ± 98 ** ||| |

$P < 0.01$; * $P < 0.001$, compared to normal saline.
||| $P < 0.001$, compared to caffeine.
••• $P < 0.001$, compared to diazepam.

5.3 Effects on Sodium Pentobarbital-induced Sleeping Time

A preliminary study was performed to find a dose level at which sodium pentobarbital would induce sleep in 100% of the animals. This dose was 40 mg/kg.

Mice were randomly divided into 5 groups of 10 mice each. They were assigned to three TTX groups at doses of 2.5, 5.0, and 10 μg/kg, respectively, one positive control (diazepam 2.5 mg/kg) group, and one blank control (normal saline) group. Injections were given to the mice of each group intraperitoneally, and then sodium pentobarbital 40 mg/kg was injected to the mice of all groups at 10 to 15 minutes before the peak effects of TTX or diazepam were manifested. The latency of righting reflex was recorded in order to determine whether or not the test drug was able to prolong the sodium pentobarbital-induced sleeping time in mice. The differences of the latencies between the TTX groups and the control groups were compared, and t-test was used to determine whether these differences were significant or not.

The results demonstrated that, with respect to the effect of prolonging the sodium pentobarbital-induced sleeping time, TTX 2.5 μg/kg, 5.0 μ/kg and 10 μg/kg groups were not significantly different from the control (normal saline) group ($P>0.05$), but were significantly different from the positive control group (diazepam) ($P<0.001$). The results are shown in Table 19.

TABLE 19

Effects of Tetrodotoxin (TTX) on the sodium pentobarbital-induced sleeping time in mice

| Drugs | Dose levels | Number of animals | Sleeping time ($\bar{X} \pm$ SD) min |
|---|---|---|---|
| Normal saline | | 10 | 33.3 ± 14.5 *** ||| |
| diazepam | 2.5 mg/kg | 10 | 146.2 ± 53. ||| |
| TTX | 2.5 μg/kg | 10 | 35.1 ± 26.2 ||| |
| TTX | 5.0 μg/kg | 10 | 36.3 ± 16.7 ||| |
| TTX | 10 μg/kg | 10 | 26.6 ± 22.5 ||| |

*** $P < 0.001$, Compared to normal saline.
||| $P < 0.001$, Compared to diazepam.

5.4 Effects on Skeletal Muscle Relaxation in Mice

Mice were randomly divided into five groups of ten mice each. They were assigned to three TTX groups at doses of 2.5, 5.0, and 10 μg/kg, respectively, one positive control (diazepam 5 mg/kg) group, and one blank control (normal saline) group. The mice were put on a metal net placed at 50 degrees to horizontal level on a table and allowed to move freely on the net. Those that did not fall from the net for an hour were considered qualified and were selected. Next, respective injections were given to the mice of each group; and the animals were again put on the net and allowed to move freely. They were observed for the following 50 minutes, and those that fell off were put back on the net. The injected drug would be considered effective in producing skeletal muscle relaxation if a mouse fell down three times consecutively. The results showed that with regard to the ability to produce skeletal muscle relaxation, TTX 2.5 μg/kg, 5.0 μg/kg and 10 μg/kg groups were not significantly different from the blank control (normal saline) group ($P>0.05$), but were significantly different from the positive control (diazepam) group ($P<0.001$). The results are shown in Table 20.

TABLE 20

Effects of Tetrodotoxin (TTX) on the skeletal muscle relaxation (climbing-net method)

| Drugs | Dose levels | Number of animals | Number of positively effected animals |
|---|---|---|---|
| Saline | — | 10 | 0 |
| Diazepam | 5 mg/kg | 10 | 8 *** |
| TTX | 2.5 μg/kg | 10 | ||| |

TABLE 20-continued

Effects of Tetrodotoxin (TTX) on the skeletal
muscle relaxation (climbing-net method)

| Drugs | Dose levels | Number of animals | Number of positively effected animals |
|---|---|---|---|
| TTX | 5.0 μg/kg | 10 | ||| |
| TTX | 10 μg/kg | 10 | ||| |

*** P < 0.001, Compared to normal saline.
||| P < 0.001, Compared to diazepam.

5.5 Effects on the Cardiovascular and Respiratory Systems of Anesthetized Dogs

Healthy hybrid dogs, half male and half female, body weight 10–15 kg, were used in this test. The dogs were anesthetized by injecting sodium pentobarbital intravenously at 30 mg/kg. Next, they were mounted in a supine position, and the femoral artery was surgically exposed and a tube was inserted for monitoring the artery blood pressure. The femoral vein of the other hind limb was surgically exposed for transfusion of nutritional fluid. The respiratory rate and depth were monitored by putting a TR-61ZT Nasal-Clipping Energy Exchanger in the nostrils. Cardiac function was monitored with a 2-lead electrocardiogram with needle electrodes. All the monitored parameters were recorded synchronously with a RM-6000 Multi-lead Recorder.

After the surgical operation, the system was stabilized for 30 minutes or more till the monitored parameters became steady, then they were recorded as the values before dosing of TTX injection. The dogs were injected im. in the buttocks with TTX preparations or an equal volume of normal saline for the blank control group, respectively. The same parameters were recorded at 15, 30, 45, 60, 90, 120 and 180 minutes after dosing.

The results showed that TTX at 1 μg/kg, 2 μg/kg, or 4 μg/kg by intramuscular injection did not significantly affect the blood pressure, heart rate, electrocardiogram or respiratory rate and depth ($P>0.05$).

Example 6
Drug Safety Studies with TTX

Kunming mice and Wistar rats were used in these studies. Age: 40 days for mice, and seven weeks for rats. Sex: half of each sex for both. Body weight: 18–20 g for mice; 130–170 g for rats. Dosing volume: 0.1 mL/10 g for mice; 0.2 mL/100 g for rats.

Material: tetrodotoxin pure powder, manufactured by Nanning Maple Leaf Pharmaceutical Co., Ltd.

6.1 Acute Toxicity of TTX in Mice

Test material: Tetrodotoxin powder, batch no. ML-003, supplied by Nanning Maple Leaf Pharmaceutical Co., Ltd.

The mice were fasted for 12 hours, then were randomly assigned to different dose groups based upon body weight, 10/sex/group. After TTX was injected by different routes (iv, ip, sc,), the reactions of each animal were immediately observed, and observation continued for one week afterwards, with toxic reactions and distribution of deaths recorded. Autopsy was performed immediately after any incident of death and pathologic changes recorded. Microscopic pathological examinations were conducted on those animals that had any changes observed during gross examinations. The $LD_{50}$ values with 95% confidence interval (CI) were calculated according to the Bliss method.

The results showed that any toxic reactions were similar regardless of administration routes. The major clinical signs were weakness of hind limbs, prostration, dyspnea, and death from respiration failure. Generally the death occurred within 1–15 min after dosing by the intravenous route, and 20–60 min by other routes. The deaths were not sex-dependent. The surviving mice recovered in about one hour after dosing. No other anomalies or deaths occurred in the surviving animals during the 7-day observation period. No abnormalities were found during the autopsy of dead animals. Distribution of deaths and determination of the $LD_{50}$ values are shown in Tables 21, 22 and 23.

TABLE 21

Distribution of death and $LD_{50}$ after a single i.v. injection of TTX in mice.

| Dose (μg/kg) | Log-arithmic Dose (x) | Number of animals | Number of deaths | Death rate | Probability unit (y) | Value of $LD_{50}$ (95% CI) |
|---|---|---|---|---|---|---|
| 11.8 | 1.070 | 10 | 10 | 1.000 | 7.038 | |
| 10.0 | 1.000 | 10 | 7 | 0.700 | 5.493 | 8.3 |
| 8.5 | 0.929 | 10 | 5 | 0.500 | 5.000 | |
| 7.2 | 0.859 | 10 | 3 | 0.300 | 4.479 | (7.5 ~ 9.2) |
| 6.1 | 0.788 | 10 | 1 | 0.100 | 3.722 | |

TABLE 22

Distribution of death and $LD_{50}$ after a single i.p. injection of TTX in mice.

| Dose (μg/kg) | Log-arithmic Dose (x) | Number of animals | Number of deaths | Death rate | Probability unit (y) | Value of $LD_{50}$ (95% CI) |
|---|---|---|---|---|---|---|
| 11.8 | 1.072 | 10 | 9 | 0.900 | 6.197 | |
| 10.0 | 1.000 | 10 | 8 | 0.800 | 5.827 | 9.0 |
| 8.5 | 0.929 | 10 | 4 | 0.400 | 4.474 | |
| 7.2 | 0.857 | 10 | 1 | 0.100 | 3.719 | (8.2 ~ 9.8) |
| 6.1 | 0.792 | 10 | 0 | 0.000 | 2.464 | |

TABLE 23

Distribution of death and $LD_{50}$ after a single s.c. injectin of TTX in mice.

| Dose (μg/kg) | Log-arithmic Dose (x) | Number of animals | Number of deaths | Death rate | Prob-ability unit (y) | Value of $LD_{50}$ (95% CI) |
|---|---|---|---|---|---|---|
| 22.9 | 1.360 | 10 | 10 | 1.000 | 7.246 | |
| 19.5 | 1.290 | 10 | 8 | 0.800 | 5.835 | 16.2 |
| 16.5 | 1.217 | 10 | 5 | 0.500 | 5.000 | |
| 14.1 | 1.149 | 10 | 2 | 0.200 | 4.163 | (14.7 ~ 17.8) |
| 12.0 | 1.079 | 10 | 1 | 0.100 | 3.734 | |

6.2 Acute Toxicity of TTX in Rats

Test material: Tetrodotoxin powder, batch no. 000530, supplied by Nanning Maple Leaf Pharmaceutical Co., Ltd.

Wistar rats were fasted for 12 hours, then randomly assigned to different dose groups based upon body weight, 5/sex/group. The test method was the same as the acute toxicity study in mice.

The result showed that approximately 10–20 minutes after i.m. injection, the rats exhibited various degrees of weakness in hindlimbs, accelerated respiration and prostration. Those with strong reactions showed serious dyspnea (Cheyne-Stokes respiration) till they died of respiratory failure generally within 1 hour after the injection. The surviving animals indicated inhibitory status and gradually recovered about 1 hour after dosing. The observation was continued for seven days and no other abnormalities or incidents of death were observed. In general, no abnormality was found during the autopsy of the dead animals.

Distribution of deaths and determination of the $LD_{50}$ values are shown in Table 24.

TABLE 24

Distribution of deaths and $LD_{50}$ after a single im. injection of TTX in rats.

| Dose (μg/kg) | Log-arithmic Dose (x) | Number of animals | Number of deaths | Death rate | Prob-ability unit (y) | Value of $LD_{50}$ (95% CI) |
|---|---|---|---|---|---|---|
| 13.72 | 1.14 | 10 | 10 | 100 | 7.49 | |
| 12.35 | 1.09 | 10 | 8 | 80 | 5.82 | 11.11 |
| 11.11 | 1.05 | 10 | 5 | 50 | 5.00 | |
| 10.00 | 1.00 | 10 | 2 | 20 | 4.18 | (10.5 ~ 11.7) |
| 9.00 | 0.96 | 10 | 0 | 0 | 2.51 | |

6.3 Sub-acute (28 Days) Toxicity Study of TTX in Rhesus Monkeys

Animals

20 Rhesus monkey, ten per sex, 3–4 years of age, body weight: ♂ 6.3±0.5 kg; ♀ 8.4±0.4 kg.

Test Material

Test material: tetrodotoxin injection, 30 μg/2 mL/ampoule, batch no.931220, supplied by Guangxi Asia Health Medical Co., Ltd. Monkeys were randomly divided into 5 groups. Three groups were given TTX (1 μg/kg, 2.5 μg/kg or 6.25 μg/kg). Another two groups were given normal saline (blank control) and 0.02% acetic acid solution (solvent control). All the test drugs were injected once a day for 28 consecutive days. Following dosing, the general behavior was monitored and recorded daily, the food intake and body weight were measured weekly. 24 hours after the last dose, blood samples were taken from the heart and used for determination of 13 hematological parameters and 15 blood biochemical parameters. 24 hours after the last dosing, one male and one female monkey of each group were killed and blood was sampled for hematological, blood biochemical, and pathological examinations. The remaining monkeys in each group were observed continuously for four weeks and then killed to conduct the same examinations above so as to know whether there could be recovery from any observed toxicity reactions and whether a delayed toxicity reaction could be manifested.

The results showed that the monkeys in the TTX 6.25 μg/kg group had evident toxic symptoms after each dosing. The major toxic reaction was vomiting. One monkey of this group showed eyelid swelling, slight paralysis and an abnormal increase in ALT and ALP values. One monkey in the TTX 2.5 μg/kg group displayed slight vomiting and AChE activity was decreased by 41.2%. There were no drug-related abnormalities found in the observations of general physiology parameters, histopathological, hematological, blood biochemical and ophthalmologic examinations in the TTX 1.0 μg/kg, blank and solvent control groups. Local muscle necrosis at the injection site of dilute acetic acid solution was found during microscopic evaluation of monkeys killed on Day 28. At the end of the recovery period (Day 56), no muscle necrosis was observed. Under the conditions of this study, the nontoxic dose level of TTX in Rhesus monkey was 1.0 μg/kg.

Example 7
Local Toxicity Study on TTX

Test material: tetrodotoxin injection, 30 μg/2 mL/ampoule, batch no.931220, supplied by Guangxi Asia Health Medical Co., Ltd.

7.1 Local Intramuscular Irritation Test in Rabbits

Eight New Zealand white rabbits, male, 13–18 weeks old, body weight 2.0–2.5 kg, were randomly divided into four groups as tetrodotoxin (0.56 μg/kg) in acetic acid, tetrodotoxin (0.56 μg/kg) in normal saline, 0.02% acetic acid control, and penicillin G-K positive control.

Before dosing, the rabbit's hair around the injection site is cut short with 3×2 cm in the injection site. The injection was done in the middle part of the quadriceps muscles in the left and right thighs of a rabbit, 1 mL each side respectively. Immediately after dosing, signs of flaccid hair, listlessness, anorexia, and mobility difficulties were monitored and recorded. At 48 hours, rabbits were sacrificed and the quadriceps muscles were taken out and incised longitudinally so as to observe local stimulation reaction in the injection sites and perform pathological examinations. The stimulation reactions were graded based upon the following evaluation criteria: 0, no obvious change, 1, slight hyperemia, in an area less than 0.5×1.0 cm, 2, medium hyperemia, in an area larger than 0.5×1.0 cm, 3, serious hyperemia, in addition with muscle degeneration, 4, necrosis manifested with brown-colored degeneration, 5, massive necrosis manifested.

The test results show that tetrodotoxin at 0.56 μg/kg in dilute acetic acid, 0.02% dilute acetic acid (solvent), and penicillin G-K at $1.54 \times 10^5$ unit/kg (positive control) produced pronounced stimulation reactions in local muscles of rabbits, while tetrodotoxin at 0.56 μg/kg in normal saline did not. Based upon these results it can be concluded that the stimulus was 0.02% dilute acetic acid rather than tetrodotoxin at the tested concentration (Table 25).

TABLE 25

Evaluation grades for the results of the local muscular stimulation tests of rabbits with tetrodotoxin

| | Grades for stimulation reaction in rabbits' quadriceps femoris muscles | | | | |
|---|---|---|---|---|---|
| | Left side | | Right side | | Sum of |
| Groups | 2 | 1 | 1 | 2 | grades |
| Tetrodotoxin in dilute acetic acid | 4 | 4 | 4 | 4 | 16 |
| Tetrodotoxin in normal saline | 0 | 0 | 0 | 0 | 0 |
| 0.02% acetic acid (excipient) | 4 | 4 | 4 | 4 | 16 |
| Penicillin G-K (positive control) | 4 | 4 | 4 | 4 | 16 |

*Number of tested rabbits 7.2 General Hypersensitivity Test in Guinea Pigs

Twenty four Hartley guinea pigs, half of each sex, 8~12 weeks old, 250~300 g, randomly assigned to three groups as a tetrodotoxin 0.95 μg/kg group, a 10% bovine serum albumin solution (positive control) group and a 0.02% dilute acetic acid group (solvent control).

Sensitization Method

In the tetrodotoxin group, each guinea pig was injected intraperitoneally 0.5 mL of the prepared tetrodotoxin sensitizing dose, once every other day for three consecutive injections. The same dosing method was used in the solvent group and the 10% bovine serum albumin (positive control) group. Afterwards the animals of each group were divided into two sub-groups with four animals per sub-group.

Stimulation Method

In each group, the animals of the first sub-group were injected intravenously with 1.0 mL of the prepared stimulation dose at the outer side of a hind limb 14 days following the sensitization dose (i.p.). The animals of the second sub-group were given the same dose by the same route on Day 21 after they were given the sensitizing dose (i.p.). The experimental animals were instantly observed for indications of hypersensitive reactions such as scratching nose, sneezing, pilo-erection, convulsion, dyspnea, fecal and urinary incontinence, shock and death, etc. Evaluating standards of test results is following: (−) No abnormal reaction, (±) Twist, pilo-erection, (+) Scratching nose, pilo-erection, uneasiness, sneezing, shortness of breath, and mild cyanosis, (++) Pilo-erection, manifest dyspnea, cyanosis, weakness of limbs, and creeping with abdomen on ground, (+++) Death.

The test results indicated that tetrodotoxin at a dose of 0.95 μg/kg and 0.02% dilute acetic acid (excipient) after stimulating did not produce pronounced general hypersensitivity reactions in guinea pigs, while the positive control, 10% bovine serum solution, induced hypersensitive reactions to various extents, such as scratching noses, pilo-erection, uneasiness, sneezing, and death of one guinea pig several minutes after stimulating (Table 26).

The test results demonstrated that tetrodotoxin at a dose level of 0.95 μg/kg did not produce general hypersensitivity reactions in guinea pigs; therefore it is safe to use this drug at this dose level.

TABLE 26

Results of general hypersensitivity test of tetrodotoxin in guinea pigs

| Groups | Hypersensitive reactions of animals | | | |
|---|---|---|---|---|
| | *− | + | ++ | +++ |
| Tetrodotoxin | 8/8 | 0/8 | 0/8 | 0/8 |
| 0.02% dilute acetic acid (solvent) | 8/8 | 0/8 | 0/8 | 0/8 |
| 10% bovine serum albumin (positive control) | 0/8 | 4/8 | 3/8 | 1/8 |

Note:
*(−) No abnormal reaction 7.3 Haemolyzation and Vascular Stimulation Tests 15 New Zealand white rabbits, 14–18 weeks old, 2.0–4.0 kg. No gender limitations.

Haemolyzation Test

Seven milliliters of rabbit blood were taken to prepare of 2% red blood cell (RBC) suspension in normal saline for experiment use. Two milliliter 0.02% acetic acid aqueous solution was used as control. Seven test tubes were put in 2% RBC suspension and normal saline and added in various amounts of the TTX. The tubes were shaken to mix the solutions evenly, and placed into a 37° C. incubator, observed and recorded at 15 minutes for the first time, and the recording was repeated subsequently every hour up to four hours.

The result showed that tetrodotoxin did not induce in vitro haemolyzation.

Vascular Stimulation Test 15 rabbits were randomly assigned to three groups as a tetrodotoxin 1.0 μg/kg group, a 0.02% acetic acid aqueous solution (solvent control) and a normal saline control group.

All groups were given one injection daily intravenously for 10 consecutive days. At 24 hours after dosing, three animals from each group were sacrificed, and the blood vessels of the injection sites were taken to conduct pathological examinations. The remaining animals were observed for two weeks; then sacrificed, and the blood vessels of the injection sites were taken to conduct pathological examinations accordingly.

The results showed that during the dosing period and afterwards, no abnormalities were observed in the mental states, body weights, body temperatures, and food intake of the treated animals, indicating that tetrodotoxin (1.0 μg/kg) by daily intravenous injection did not produce any pronounced vascular stimulation in rabbits.

Example 8

Teratogenic Effect of Tetrodotoxin in Mice by Intramuscular Injection

Test Material

Tetrodotoxin injection, 30 μg/2 mL/ampoule, batch no.931220, supplied by Guangxi Asia Health Medical Co., Ltd.

Animal

Shanghai mice, 250 female and 80 male, 80~100 days, healthy, sexually mature, nulliparous and never fertilized. Body weight: Female: 25~35 g. Male: 30~40 g.

The mice were randomly divided into three TTX groups (2.5, 5.0 and 10.0 μg/kg), a positive control group (cyclophosphamide, 20 mg/kg), a solvent control group (0.02% dilute acetic acid) and a blank control group (water for injection).

One injection (i.m.) was given once daily to each female from day 6 to day 15 of gestation in all groups but the positive control group in which a single injection was given to each female mouse on day 11 of gestation. Male animals were not dosed.

The results showed that during the treatment period the general conditions of pregnant mice were fine. No abnormal signs were found in the pregnant mice after dosing. No embryotoxicity or teratogenic action was found in Shanghai mice treated with tetrodotoxin at dose levels of 2.5, 5.0 and 10.0 μg/kg, equal to ⅛, ¼ and ½ $LD_{50}$, respectively, one injection (i.m.) daily from day 6 to day 15 of gestation. Neither was malformation found in external, visceral and skeletal structures of those animals treated with either 0.02% dilute acetic acid (solvent control) or water for injection. However, the teratogenic rate was 100% when a single injection of cyclophosphamide (CP) was given to pregnant mice on day 11. This study evidenced that tetrodotoxin has no embryotoxicity or teratogenic effect on Shanghai mice.

Example 9

9.1 Mutagenicity Test in the Salmonella (Ames Test)

Test material: Tetrodotoxin powder, batch no. 940701, supplied by Dalian Ao Sen Pharmaceutical Plant, Liaoning, China.

The mutagenicity potential of tetrodotoxin to four standard test Salmonella strains was studied using the preincubation procedure of the plate incorporation test. The results indicated that tetrodotoxin at the concentrations of 0.01 to 100.0 (of the maximum solubility) μg/plate did not induce any increase in mutation rates of four strains (TA97, TA98, TA100 and TA102) both in the presence and absence of $S_9$ activation. This suggested that tetrodotoxin was not mutagenic to the Salmonella strains.

The results of the mutagenicity tests on the test drug, tetrodotoxin, and the positive controls in the Salmonella are displayed in Table 27 and Table 28.

TABLE 27

Results of the mutagenicity test on positive control in the Salmonella

| Concentration | S₉ | Number of revertant Salmonella colonies (per | | | |
|---|---|---|---|---|---|
| | | TA97 | TA98 | TA100 | TA102 |
| 0.0 | − | 138 ± 18 | 36 ± 5 | 130 ± 11 | 270 ± 45 |
| | + | 116 ± 27 | 40 ± 11 | 154 ± 21 | 263 ± 10 |
| Dexon (50.0) | − | 1567 ± 315 | 604 ± 86 | 562 ± 50 | 858 ± 79 |
| DMSO | + | 126 ± 41 | 30 ± 5 | 129 ± 17 | 242 ± 10 |
| 2-AF (40.0) | − | 97 ± 17 | 26 ± 7 | 97 ± 13 | |
| | + | 1293 ± 366 | 1538 ± 335 | 1795 ± 303 | |
| DAN (100.0) | − | | | | 379 ± 99 |
| | + | | | | 906 ± 69 |

TABLE 28

Results of the mutagenicity test on tetrodotoxin in the Salmonella

| Concentration | S₉ | Number of revertant Salmonella colonies (per | | | |
|---|---|---|---|---|---|
| (μg/plate) | | TA97 | TA98 | TA100 | TA102 |
| 0.0 | − | 138 ± 1 | 36 ± 5 | 130 ± 11 | 270 ± 45 |
| Solvent* | − | 122 ± 1 | 30 ± 8 | 140 ± 12 | 281 ± 53 |
| 0.01 | − | 126 ± 9 | 37 ± 15 | 132 ± 15 | 273 ± 42 |
| 0.10 | − | 110 ± 1 | 31 ± 9 | 123 ± 25 | 290 ± 34 |
| 1.0 | − | 114 ± 2 | 32 ± 10 | 131 ± 17 | 301 ± 66 |
| 10.0 | − | 114 ± 1 | 36 ± 4 | 131 ± 18 | 282 ± 63 |
| 100.0 | − | 126 ± 1 | 30 ± 8 | 139 ± 11 | 292 ± 55 |
| 0.0 | + | 116 ± 2 | 40 ± 11 | 154 ± 21 | 263 ± 10 |
| Solvent* | + | 106 ± 1 | 38 ± 13 | 147 ± 15 | 277 ± 28 |
| 0.01 | + | 142 ± 1 | 46 ± 11 | 142 ± 18 | 280 ± 25 |
| 0.10 | + | 114 ± 2 | 44 ± 19 | 139 ± 17 | 266 ± 30 |
| 1.0 | + | 110 ± 2 | 42 ± 13 | 130 ± 17 | 299 ± 51 |
| 10.0 | + | 108 ± 2 | 43 ± 8 | 149 ± 14 | 276 ± 33 |
| 100.0 | + | 119 ± 3 | 44 ± 8 | 127 ± 16 | 273 ± 28 |

*0.02 dilute acetic acid.

As shown in Table 29, the diagnostic direct mutant, Dexon, and indirect mutants, 2-AF and DAN, all caused a significant increase in the number of revertant colonies of tested strains, twice or more times as compared to the negative control groups. This evidenced the reliability of the selected research system. Tetrodotoxin at concentrations of 0.01 to 100 μg/plate did not cause any significant increase in the number of revertant colonies of four tested strains, either in the presence or absence of S₉ activation. This suggested that tetrodotoxin is not mutagenic to the Salmonella strains.

9.2 Chromosomal Aberration Test in CHL Cells

Test material: Tetrodotoxin powder, batch no. 940701, supplied by Dalian Ao Sen Pharmaceutical Plant, Liaoning, China.

The Chinese hamster lung (CHL) cells were exposed to tetrodotoxin at the concentrations of 5.0, 10.0, and 20.0 μg/mL for 24 or 48 hours in the absence of $S_g$ activation and for 6 hours in the presence of S₉ activation. The results suggested that tetrodotoxin did not significantly increase the chromosomal aberration rate compared to solvent control.

The test results of tetrodotoxin's aberration action on CHL cell chromosome in the absence of metabolic activation are displayed in Table 29.

TABLE 29

Tetrodotoxin's aberration action on CHL cell chromosome in the absence of metabolic activation

| Tests (μg/mL) | Cell collection time (hours) | Number of observed cells (piece) | Chromosomal aberration rate (%) |
|---|---|---|---|
| Blank control | 24 | 100 | 0 |
| Solvent control | 24 | 100 | 3 |
| Tetrodotoxin | | | |
| 5.0 | 24 | 100 | 0 |
| 10.0 | 24 | 100 | 0 |
| 20.0 | 24 | 100 | 2 |
| MMC | | | |
| 0.25 | 24 | 100 | 72** |
| Blank control | 48 | 100 | 0 |
| Solvent control | 48 | 100 | 2 |
| Tetrodotoxin | | | |
| 5.0 | 48 | 100 | 1 |
| 10.0 | 48 | 100 | 2 |
| 20.0 | 48 | 100 | 1 |
| MMC | | | |
| 0.25 | 48 | 100 | 99** |

**By comparison with the solvent control group, P < 0.01.

As shown in Table 29, at 24 hours and 48 hours after exposure, chromosomal aberration rates of the blank control group were both 0%; that of the solvent control group, 3% and 2%, respectively; those of tetrodotoxin at concentrations of 5.0–20.0 μg/mL, 0–2%. Structural aberrations were found in the chromosomes. The aberration rates of the positive control MMC group were 72% and 99% at 24 hours and 48 hours after exposure, respectively (P<0.01).

The observed results of tetrodotoxin's aberration action on CHL cell chromosome in the presence of metabolic activation are displayed in Table 30.

TABLE 30

Tetrodotoxin's aberration action on CHL cell chromosome in the presence of metabolic activation

| Tests (μg/mL) | S₉ mixture (mL) | Time of cell collecting (hours) | Number of observed cells (piece) | Chromosomal aberration rate (%) |
|---|---|---|---|---|
| Blank control | — | 24 | 100 | 2 |
| Solvent control | — | 24 | 100 | 1 |
| Solvent control | 0.5 | 24 | 100 | 1 |
| S₉ control | 0.5 | 24 | 100 | 1 |
| Tetrodotoxin | | | | |
| 5.0 | 0.5 | 24 | 100 | 0 |
| 10.0 | 0.5 | 24 | 100 | 3 |
| 20.0 | 0.5 | 24 | 100 | 0 |
| CP | | | | |
| 20.0 | — | 24 | 100 | 0 |
| 20.0 | 0.5 | 24 | 100 | 50** |
| Blank control | — | 48 | 100 | 2 |
| Tetrodotoxin | | | | |
| 5.0 | 0.5 | 48 | 100 | 1 |
| 10.0 | 0.5 | 48 | 100 | 1 |
| 20.0 | 0.5 | 48 | 100 | 1 |
| CP | | | | |
| 20.0 | — | 48 | 100 | 3 |
| 20.0 | 0.5 | 48 | 100 | 42** |

**By comparison with the S₉ control group, P < 0.01.

As shown in Table 30, at 24 hours and 48 hours exposure, chromosomal aberration rates of the blank control group were both 2%; those of the solvent control groups, 1%, 2%, respectively; those of solvent control in the presence of $S_9$, 1% and 3%, respectively; those of $S_9$ control, 1% and 3% respectively. For tetrodotoxin groups, the chromosomal aberration rates fell between 0% 3% at concentrations of 5.0~20.0 μg/mL. Structural aberrations were found in the chromosomes. The chromosomal aberration rates of the positive control CP group were 50% and 42% respectively (P<0.01), whereas they were 0% and 3% respectively in the absence of metabolic activation.

The above results indicated that in the absence of metabolic activation the chromosomal aberration rates of the blank control group, the solvent control group, the tetrodotoxin groups at the concentration range of 5.0~20.0 μg/mL fell within the normal range, whereas those of the positive control MMC group manifested significant increases. In the presence of metabolic activation the chromosomal aberration rates of the blank control group, the solvent control group, the solvent plus $S_g$ control group, $S_g$ control group, the tetrodotoxin groups at the concentration range of 5.0~20.0 μg/mL also fell within the normal range, whereas those of the positive control CP group manifested significant increases. Similarly, the aberration rates of the positive control CP group fell within the normal range in the absence of metabolic activation. These results evidenced the reliability of this test system. Therefore, tetrodotoxin at the concentration range of 5.0~20.0 μg/mL did not induce chromosomal aberrations in CHL cells.

9.3 Micronucleus Test on Tetrodotoxin in Mouse's Marrow Cells

Test material: tetrodotoxin injection, 30 μg/2 mL/ampoule, batch no.931220, supplied by Guangxi Asia Health Medical Co., Ltd. Three dose groups, tetrodotoxin 10, 5 and 2.5 μg/kg, were assigned in this test. The route of administration was intramuscular injection (Induction). Two control groups were assigned: one was solvent control group of acetic acid (0.02%); and another, a positive control group of cyclophosphamide (CP, 60 mg/kg). Another group of tetrodotoxin at 10 μg/kg was also assigned to sample at 12 hours, 24 hours, 36 hours, 48 hours and 72 hours after drug dosing, while for all other groups specimens were made at 24 hours after the first dosing, so as to examine their micronucleus rates. The results indicated that after dosing/induction the micronucleus rate of tetrodotoxin at 10 μg/kg was 4.3%, which was significantly different from that of the solvent control group (P<0.05), whereas the micronucleus rate of the positive control group was 46.5%, highly significantly different from that of the solvent control group (P<0.01). TTX at 5 and 2.5 μg/kg did not cause any considerable changes.

The micronucleus rates of the mice given tetrodotoxin at 10 μg/kg at 12 hours, 24 hours, 36 hours, 48 hours, and 72 hours after dosing are displayed in Table 31. The results of all groups fell within normal range. Based upon above results, the time to sacrifice animals for preparing specimens was to be determined at 24 hours after the first dosing.

TABLE 31

Micronucleus rates of mice dosed tetrodotoxin at 10 μg/kg at various time points

| Time Point (hour after dosing) | Number of polychromatic erythrocyte | Number of Micronucleus cells | Micronucleus rate (%) ($\overline{X} \pm SD$) |
|---|---|---|---|
| 12 | 6000 | 22 | 3.7 ± 2.2 |
| 24 | 6000 | 8 | 1.3 ± 1.0 |
| 36 | 6000 | 18 | 3.0 ± 1.1 |
| 48 | 6000 | 16 | 3.3 ± 1.3 |
| 72 | 6000 | 24 | 4.0 ± 2.5 |
| Solvent 24 | 6000 | 13 | 2.2 ± 0.8 |

The results of those animals given tetrodotoxin at 10, 5 and 2.5 μg/kg are displayed in Table 32. The micronucleus rate of tetrodotoxin at 10 μg/kg was 4.3‰, which was statistically different from that of the solvent control (P<0.05). The micronucleus rates of other groups fell within the normal range, while that of the positive control was highly significantly different from that of the solvent control (P<0.01).

TABLE 32

Micronucleus rates of the mice in all groups

| Dose (μg/kg) | Number of polychromatic erythrocyte | Number of Micronucleus cells | Micronucleus rate (%) ($\overline{X} \pm SD$) |
|---|---|---|---|
| 10 | 6000 | 26 | 4.3 ± 1.6* |
| 5 | 6000 | 15 | 2.5 ± 1.5 |
| 2.5 | 6000 | 13 | 2.2 ± 1.3 |
| Solvent | 6000 | 13 | 2.2 ± 0.8 |
| CP (60 μg/kg) | 6000 | 279 | 46.5 ± 12.8** |

*By comparison with the solvent group, P < 0.05
**By comparison with the Solvent group, P < 0.01

Under the conditions of this test, such as dosage level, route of administration and dosing plan, the results indicated that the micronucleus rates induced by intramuscular injection of tetrodotoxin at 10 μg/kg increased slightly and were statistically different from that of the solvent control (P<0.05). The micronucleus rates induced by tetrodotoxin at 2.5 and 5 μg/kg (im.) fell within the normal range, whereas that by the positive control was highly significantly different from that of the solvent control (P<0.01). These results evidenced reliability of this experimental system.

The results of the experiment indicated that tetrodotoxin at high dose level, 10 μg/kg that is equal to ½ $LD_{50}$, had some effect on mouse micronucleus rate, but this is not of clinical significance because this dose is much higher than those of clinical use. To further examine such effect of tetrodotoxin, we carried out some supplemental studies (please refer to the following attachment).

Attachment

To further examine tetrodotoxin's effect on mouse micronucleus rate, we carried out a supplemental test with results displayed in Tables 33 and 34.

TABLE 33

Effect of dosing frequency of tetrodotoxin on micronucleus rate*

| Tetrodotoxin Dose ($\mu$g/kg) | Route of administration | Micronucleus rate (‰ ± SD) | |
|---|---|---|---|
| | | Single injection | Inductive dosing** |
| 0 | i.m. | 2.2 ± 0.8 | 2.2 ± 0.8 |
| 2.5 | i.m. | 1.3 ± 1.7 | 2.2 ± 1.3 |
| 5.0 | i.m. | 1.7 ± 2.1 | 4.0 ± 1.6 |
| 10.0 | i.m. | 1.8 ± 1.8 | 5.8 ± 2.4*** |

*Number of animals: 3 to 5 per group
**Two injections
*** $P < 0.05$ by comparison with the solvent control group.

TABLE 34

Effect of administration route of tetrodotoxin on micronucleus rate

| Tetrodotoxin Dose ($\mu$g/kg) | Route of Administration | Micronucleus rate (‰ ± SD) |
|---|---|---|
| 7 | i.m. | 4.7 ± 3.5 |
| 7 | i.p. | 4.0 ± 1.7 |

As shown in Table 33, the micronucleus rate of tetrodotoxin at high dose (10 $\mu$g/kg) by single dosing was 5.8±2.40‰, which was slightly higher than normal; whereas the micronucleus rates of tetrodotoxin at 2.5, and 5 $\mu$g/kg fell within the normal range but those by inductive dosing (two injections) were all higher than those by a single injection.

Two routes of administration, i.m. and i.p., were compared, and the results in Table 34 indicated that the micronucleus rates of these two routes were not significantly different.

Conclusively, the effect of tetrodotoxin on the marrow cell micronucleus rate of AMS mice was studied in this test. At dosage levels ranging from ½ to ⅛ $LD_{50}$, tetrodotoxin did not induce any significant increase in micronucleus rate except that the results of tetrodotoxin at ½ $LD_{50}$ were slightly higher than normal. Neither did the route of administration statistically make any differences in the micronucleus rates.

It is understood that the foregoing description and specific embodiments shown herein are mere illustrative of the best mode of the invention and the principles thereof. Modifications and additions to the invention may easily be made by those skilled in the art without departing from the spirit and scope of the invention, which is therefor understood to be limited only by the scope of the appended claims.

Articles of the scientific periodical and patent literature cited herein are hereby incorporated by reference in their entirety and for all purposes.

We claim:

1. A method for producing analgesia in a mammal experiencing pain comprising systemically administering an amount of a composition comprising a sodium channel blocking compound, in a suitable pharmaceutical vehicle, effective to alleviate the pain.

2. The method of claim 1, wherein the sodium channel blocking compound is one selected from the group consisting of tetrodotoxin, anhydrotetrodotoxin, tetrodaminotoxin, methoxytetrodotoxin, ethoxytetrodotoxin, deoxytetrodotoxin and tetrodonic acid.

3. The method of claim 1, wherein the systemic administration is performed by intramuscular injection, subcutaneous injection, intravenous injection, oral ingestion, sublingual ingestion, skin patch, implantable osmotic pump, collagen implant, aerosol inhalation, or suppository.

4. The method of claim 1, wherein the pain is caused by mechanical, chemical or ischemic stimulation, or inflammation.

5. The method of claim 1, wherein the pain is neuropathic pain.

6. The method of claim 1, wherein the pain arises from cancer.

7. The method of claim 1, wherein the sodium channel blocking compound is administered in a dose of 0.1 to 5 $\mu$g per kilogram body weight.

8. The method of claim 1, wherein the composition is administered in one or more doses per day during a treatment period.

9. The method of claim 1, wherein the sodium channel blocking compound does not cause drug dependence or addiction in the mammal.

10. The method of claim 1, wherein the mammal is a female of childbearing age.

11. The method of claim 1, wherein the sodium channel blocking compound does not have any non-reversible adverse effects.

12. The method of claim 1, wherein the sodium channel blocking compound does not produce local intramuscular irritation at the region where the systemic administration is performed.

13. The method of claim 1, wherein the sodium channel blocking compound does not produce any general hypersensitivity reaction in the mammal.

14. The method of claim 1, wherein the sodium channel blocking compound does not induce haemolyzation or vascular stimulation in the mammal.

15. The method of claim 3, wherein the injectable formulation is administered every 3–12 hours during a treatment period.

16. The method of claim 15, wherein the treatment period is 1 to 10 days, preferably 3 days.

17. The method of claim 15, wherein the treatment is repeated.

18. The method of claim 3, wherein said the administration is by injection and the composition comprises an acetic acid solution of tetrodotoxin.

19. The method of claim 1, wherein the sodium channel blocking compound comprises a tetrahydropurine moiety comprising two guanidine units fused together in a stable azaketal linkage, having a molecular formula $C_{10}H_{17}N_7O_4$, (mol. wt. 299.30) or a derivative thereof.

20. The method of claim 19, wherein the sodium channel blocking compound is hydroxysaxitoxin or neosaxitoxin.

21. The method according to claim 6, wherein the pain arises from a cancer selected from the group consisting of liver cancer, rectal cancer, leiomyosarcoma, bone cancer, stomach cancer, lymphatic cancer, esophageal cancer, cancers in the genital organs, prostate cancer, digestive system cancer, stomach cancer, colon cancer, breast cancer, respiratory system cancer, lung cancer, bronchial cancer, urinary system cancer, lymphoma and skin cancer.

* * * * *

US006407088C1

(12) EX PARTE REEXAMINATION CERTIFICATE (6205th)
United States Patent
Dong et al.

(10) Number: US 6,407,088 C1
(45) Certificate Issued: Apr. 22, 2008

(54) METHOD OF ANALGESIA

(75) Inventors: Qingbin Dong, Nanning (CN); Frank Hay Kong Shum, North Point (HK)

(73) Assignee: Wex Medical Instrumentation Co., Ltd., North Point (HK)

Reexamination Request:
No. 90/007,826, Nov. 29, 2005

Reexamination Certificate for:
Patent No.: 6,407,088
Issued: Jun. 18, 2002
Appl. No.: 09/695,053
Filed: Oct. 25, 2000

(30) Foreign Application Priority Data

Sep. 18, 2000 (CN) .......................... 00 1 24517

(51) Int. Cl.
*A61K 31/506* (2006.01)
*A61K 31/517* (2006.01)
*A61K 31/519* (2006.01)

(52) U.S. Cl. .................. 514/183; 514/257; 514/267; 514/282

(58) Field of Classification Search .............. None
See application file for complete search history.

(56) References Cited

U.S. PATENT DOCUMENTS 1,058,643 A * 4/1913 Tahara ..................... 424/554
3,898,339 A    8/1975 Adams et al.

FOREIGN PATENT DOCUMENTS

| CN | 1192903 A | 9/1998 |
|---|---|---|
| CN | 1227102 A | 9/1999 |
| CN | 1356104 A * | 7/2002 |
| GB | 1370904 A * | 10/1974 |
| WO | WO 9851290 A2 * | 11/1998 |

OTHER PUBLICATIONS

Goodman and Gilman. The Pharmacological Basis of Therapeutics, Eighth Edition, 1990, p. 54.*
FDA Guidance for Industry Estimating the Maximum Safe Starting Dose in Initial Clinical Trials for Therapeutics in Adult Healthy Volunteers. 2005.*
Bower et al. Clin. Toxicol. 1981, 18(7), pp. 813, 840–841.*
Yu et al., "Experimental Study on the Analgesic Effect of Tetrodotoxin in Mice," Acta. Academae Medicinae Shandong (Jun. 1999) 37:1 20–12.*
Haegerstam, G, "Effect of IV Administration of Lignocaine and Tetrodotoxin on Sensory Units in the Tooth of the Cat," Br. J. Anaesth. (1979) 51: 487–491.*
Suehiro, M, "Historical Review on the Chemical and Medical Studies of Globefish Toxin Before World War II," J. Soc. Hist. Pharmacy (1994) 29:428–434.*
Advertisement for the marketed tetrodotoxin. Journal of Neurology, 1931.*
Kao CY. Pharmacological Reviews. 1968, 19(2):997–1049.*
Y.S. Lyu et al., Brain Research vol. 871, 2000, pp. 98–103.
D.S. Kohane et al., Anesthesiology, vol. 89, No. 1, Jul. 1998, pp. 119–131.

* cited by examiner

*Primary Examiner*—Evelyn Huang

(57) ABSTRACT

This invention relates to a method of producing analgesia in a mammal experiencing pain by systemically administering an effective amount of a composition comprising essentially of a sodium channel blocking compound, in a suitable pharmaceutical vehicle, to alleviate the pain.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 7, 9–10, 13–16 and 19 are determined to be patentable as amended.

Claims 2–6, 8, 11–12, 17–18 and 20–21, dependent on an amended claim, are determined to be patentable.

New claims 22–27 are added and determined to be patentable.

1. A method for producing analgesia in a [mammal] *human* experiencing pain comprising systemically administering *to said human* an amount of a composition comprising a sodium channel blocking compound, *that is tetrodotoxin or a derivative thereof or saxitoxin or a derivative thereof in a dosage of from 0.1 to 1.2 µg per kilogram body weight* in a suitable pharmaceutical vehicle, effective to alleviate the pain.

7. The method of claim 1, wherein the sodium channel blocking compound is administered in a dose of 0.1 to [5] *1* µg per kilogram body weight.

9. The method of claim 1, wherein the sodium channel blocking compound does not cause drug dependence or addiction in the [mammal] *human*.

10. The method of claim 1, wherein the [mammal] *human* is a female of childbearing age.

13. The method of claim 1, wherein the sodium channel blocking compound does not produce any general hypersensitivity reaction in the [mammal] *human*.

14. The method of claim 1, wherein the sodium channel blocking compound does not induce haemolyzation or vascular stimulation in the [mammal] *human*.

15. The method of claim 3, wherein [the injectable formulation] *an injection* is administered every 3–12 hours during a treatment period.

16. The method of claim 15, wherein the treatment period is 1 to 10 days[, preferably 3 days].

19. The method of claim 1, wherein the sodium channel blocking compound [comprises a tetrahydropurine moiety comprising two guanidine units fused together in a stable azaketal linkage, having a molecular formula $C_{10}H_{17}N_7O_4$, (mol. wt. 299.30)] *is saxitoxin or a derivative thereof*.

*22. The method according to claim 1, in which the composition is administered from two to four times per day.*

*23. The method of claim 16, in which the treatment period is three days.*

*24. The method of claim 15, in which the treatment is repeated after an interval of from 20 to 30 days.*

*25. The method of claim 1, in which the dosage is from 0.4 to 0.8 µg per kilogram body weight.*

*26. A method for producing analgesia in an adult human experiencing pain comprising systemically administering to said adult human an amount of a composition comprising a compound selected from the group consisting of tetrodotoxin, anhydrotetrodotoxin, tetrodaminotoxin, methoxytetrodotoxin, ethoxytetrodotoxin, deoxytetrodotoxin, tetrodonic acid, saxitoxin, hydroxysaxitoxin and neosaxitoxin in a dosage of from 20 to 40 µg of said compound in a suitable pharmaceutical vehicle, effective to alleviate the pain.*

*27. The method of claim 26, in which the sodium channel blocking compound is tetrodotoxin.*

\* \* \* \* \*